United States Patent [19]

Vari

[11] Patent Number: 5,503,559

[45] Date of Patent: Apr. 2, 1996

[54] FIBER-OPTIC ENDODONTIC APPARATUS AND METHOD

[75] Inventor: Sandor G. Vari, Encino, Calif.

[73] Assignee: Cedars-Sinai Medical Center, Los Angeles, Calif.

[21] Appl. No.: 129,408

[22] Filed: Sep. 30, 1993

[51] Int. Cl.$^6$ .............................. A61C 5/10; A61C 1/00
[52] U.S. Cl. ............................ 433/224; 433/29; 433/102
[58] Field of Search ............................ 433/29, 102, 224, 433/90; 128/665, 634; 356/317, 318, 341

[56] References Cited

U.S. PATENT DOCUMENTS

| | | | |
|---|---|---|---|
| 3,313,290 | 8/1963 | Chance et al. | 128/2 |
| 3,590,232 | 6/1971 | Sadowski | 240/2 |
| 3,614,414 | 9/1971 | Gores | 240/2 |
| 3,706,612 | 10/1971 | Clemens | 356/178 |
| 3,789,506 | 2/1974 | Johns . | |
| 3,830,222 | 8/1974 | Chance | 128/2 A |
| 3,975,098 | 8/1976 | West | 356/85 |
| 4,162,405 | 7/1979 | Chance et al. | 350/461 B |
| 4,170,987 | 10/1979 | Anselmo et al. | 128/665 |
| 4,178,917 | 12/1979 | Shapiro | 128/665 |
| 4,184,175 | 1/1980 | Mullane, Jr. | 358/93 |
| 4,212,639 | 7/1980 | Schaffner | 433/102 |
| 4,236,526 | 12/1980 | Richard | 128/633 |

(List continued on next page.)

OTHER PUBLICATIONS

Hartles et al., "The Identification of Pyrimidines in the Fluorescing Fractions of the Teeth of the Sperm Whale," J. D. Res., vol. 34, No. 6, Dec. 1955, pp. 820–830.

Hoerman et al., "Fluorometric Demonstration of Tryptophan in Dentin and Bone Protein," J. Dent. Res., vol. 43, No. 2, 3–4/64, pp. 276–280.

Fukushima et al., "Topography of Fluorescence and its Possible Composites in Human Teeth," Cell. & Molec. Bio., vol. 33(3), 1987, pp. 725–736.

Kvaal et al., "Fluorencence from detin and cementum in human mandibular second premolars and its relation to age," Scand. J. Dent. Res., 1989, pp. 97:131–138.

Per Torell, "Iron and Dental Caries," Sweden Dental Journal, 1988, pp. 12:113–124.

Hafstrom–Bjorkman et al., "Comparison of Laser Fluor. & Longitudinal Microradiography for Quantitative Assess. of in vitro Enamel Caries," Caries Res., 1992, 26:241–247.

Giunta et al., "Dentin formation in miniature pigs with special ref. to indomethacin and orthodontic treatment," Scandinavian J. of Dent. Res., 1993, 101:261–264.

Feghali–Assaly et al., "Cytokeratin profile of the junctional epithelium in partially erupted teeth," J. Periodont Res. 1994, 29:185–195.

(List continued on next page.)

Primary Examiner—Cary E. O'Connor
Attorney, Agent, or Firm—Pretty, Schroeder, Brueggemann & Clark; Edward G. Poplawski; Robroy R. Fawcett

[57] ABSTRACT

An endodontic apparatus and related method for the instant detection of the anatomical structure of a tooth and for the restoration of a dead or severely decayed tooth using induced fluorescence spectroscopy. A root canal probe having an optical fiber through its center transmits excitation light into the tooth's root canal. The excitation light induces the tissue within the root canal to fluoresce. The fluorescent light is collected by the optical fiber and transmitted back to a sensor that generates electrical signals indicative of the intensity of light within predetermined wavelength bands. The electrical signals are processed to identify the tissues within the root canal. The probe may include a slightly conical metal surface having flutes for shaving and removing dentin from within the root canal. Using the fluorescent emission properties of the tissues of components of a tooth, the entrance of the root canal is located. The root canal is cleaned and shaped and the apex of the root canal located using the difference between the fluorescence spectrum of the apex and the root canal. The root canal is sealed and filled by a light cure restorative delivered into the root canal through a tube. The light cure restorative is activated by light transmitted into the root canal by an optical fiber. The light activation and polymerization of the light cure restorative can be controlled by monitoring the intensity of the restorative's fluorescence spectrum.

31 Claims, 18 Drawing Sheets

U.S. PATENT DOCUMENTS

| | | | |
|---|---|---|---|
| 4,412,543 | 11/1983 | Vassiliadis et al. | 128/633 |
| 4,449,535 | 5/1984 | Renault | 128/634 |
| 4,479,499 | 10/1984 | Alfano | 128/665 |
| 4,569,354 | 2/1986 | Shapiro et al. | 128/633 |
| 4,608,990 | 9/1986 | Elings | 128/633 |
| 4,629,693 | 12/1985 | Khanna | 435/7 |
| 4,631,413 | 12/1986 | Jensen et al. | 250/458.1 |
| 4,675,529 | 6/1987 | Kushida | 250/458.1 |
| 4,818,229 | 4/1989 | Vasile | 433/127 |
| 4,894,547 | 1/1990 | Leffell et al. | 250/461.2 |
| 4,930,516 | 6/1990 | Alfano et al. | 128/665 |
| 4,951,669 | 8/1928 | Maxwell et al. | 128/637 |
| 4,957,114 | 9/1990 | Zeng et al. | 128/665 |
| 4,979,900 | 12/1990 | Okamoto et al. | 433/224 |
| 4,981,138 | 1/1991 | Deckelbaum et al. | 128/665 |
| 4,981,779 | 1/1991 | Wagner | 435/288 |
| 5,001,054 | 5/1991 | Wagner | 435/14 |
| 5,007,837 | 4/1991 | Werly | 433/226 |
| 5,014,707 | 5/1991 | Schwartz | 128/633 |
| 5,034,189 | 7/1991 | Cox et al. | 422/52 |
| 5,037,738 | 8/1991 | Lamos et al. | 435/12 |
| 5,042,494 | 8/1991 | Alfano | 128/665 |
| 5,046,501 | 10/1991 | Crilly | 128/665 |
| 5,072,373 | 12/1991 | Taratuta et al. | 128/633 |
| 5,074,306 | 12/1991 | Green et al. | 128/664 |
| 5,092,773 | 3/1992 | Levy | 433/224 |
| 5,093,266 | 3/1992 | Leader et al. | 436/68 |
| 5,098,298 | 3/1992 | Johnson | 433/224 |
| 5,115,137 | 5/1992 | Anderson-Engels et al. | 250/461.2 |
| 5,116,227 | 5/1992 | Levy | 433/216 |
| 5,127,405 | 7/1992 | Alcala et al. | 128/633 |
| 5,151,029 | 9/1992 | Levy | 433/29 |
| 5,172,693 | 12/1992 | Doody | 128/633 |
| 5,209,231 | 5/1993 | Cote et al. | 128/633 |
| 5,217,456 | 8/1993 | Narcisco, Jr. | 606/15 |
| 5,284,443 | 2/1994 | Weil | 433/224 |
| 5,286,193 | 2/1994 | Roane | 433/224 |

OTHER PUBLICATIONS

Parker et al., "*Metabolism of [$^3$H]–Noradrenaline in Human Dental Pulp in Vitro,*" Archs oral Biol. vol. 39, No. 1, 1994, pp. 43–49.

Yoshiba et al., "*A Confocal Laser Scanning Microscopic Study, etc.,*" Niligata Univ. School of Dent., Japan, Archs oral Biol. vol. 39, No. 5, 1994, pp. 395–400.

Patent Abstracts of Japan, vol. 015, No. 302 (C–0855), Aug. 2, 1991 & JP, A,03112549 (Matsutani Seisakusho), May 14, 1995.

Katsura et al., "*Unitraviolet Absorption of Human Teeth as Revealed by Microphotomety,*" ACTA Histochem, Cytochem, vol. 7, No. 4, 1974, pp. 328–333.

Horibe et al., "*Multiple Distribution of the Fluorescence in Human Teeth,*" ACTA Histochem, Cytochem, vol. 7, No. 4, 1984, pp. 334–341.

Willenborg, "Dental Laser Applications: Emerging to Maturity," Lasers in Surgery and Medicine, vol. 9 pp. 309–313 (1989).

Hibst et al., "Experimental Studies of the Application of the Er: YAG Laser on Dental Hard Substances," Lasers in Surgery & Medicine, vol. 9, pp. 338–351 (1989).

Pini et al., "Laser Dentistry: A New Application of Eximer Laser in Root Canal Therapy," Lasers in Surgery and Medicine, vol. 9, pp. 352–357 (1989).

Pini et al., "Laser Dentistry: Root Canal Diagnostic Technique Based on Ultraviolet–Induced Fluorescence Spectroscopy," Lasers in Surgery and Medicine, vol. 9, pp. 358–361 (1989).

Myers, "Emergence of Lasers in Dentistry," CDA Journal, vol. 19, No. 3, Mar. 1991, pp. 53–58.

Buchanan, "Paradigm Shifts In Cleaning and Shaping," CDA Journal, vol. 19, No. 5, May 1991, pp. 23–34.

Goon, "Managing the Obstructed Root Canal Space," CDA Journal, vol. 19, No. 5, May 1991, pp. 51–60.

Chess, "Laser Dentistry," CDA Journal, vol. 19, No. 11, Nov. 1991, pp. 19–23.

Myers, et al. "The Pulsed Nd: YAG Dental Laser," CDA Journal, vol. 19, No. 11, Nov. 1991, pp. 25–30.

Zakariasen, "Dental Lasers and Science," CDA Journal, vol. 19, No. 11, Nov. 1991, pp. 31–36.

Smith, "Patient Response to Dental Laser Treatment," CDA Journal, vol. 19, No. 11, Nov. 1991, pp. 37–41.

Parkins et al., "YAG Laser Treatment in Pediatric Centistry," CDA Journal, vol. 19, No. 11, Nov. 1991, pp. 43–50.

Kutsch et al., "Guided Tissue Regeneration by Intermittent Nd: YAG Laser De-Epithelialization," vol. 19, No. 11 Nov. 1991, pp. 52–58.

Biswas, "Optical Fiber Coatings for Biomedical Applications," Optical Engineering, vo. 31, No. 7, Jul. 1992, pp. 1400–1403.

Paghdiwala, "Does the Laser Work on Hard Dental Tissue?", J. Am. Dental Assoc., Jan. 1991, pp. 1, 79–80.

"Substance Identification Neural Network," Physical Optical Corp. product information, Date: unknown.

Dental Supply Cataog, Winter/Spring 1991, pp. 1, 72–73, 93.

Bassnett et al., "Intracellular pH measurement using single excitation–dual emission fluorescence ratios," Am. J. Physiol. 258, 1990, pp. C171–C178.

Ring et al., "In–Vitro Evaluation of New Fiber Optic pH, Carbon Dioxide, and Oxygen Sensor Systems," Date: unknown, 10 pages.

Ring et al., "In–Vitro Evaluation of New Fiber Optic pH, Carbon Dioxide and Oxygen Sensor Systems," SPIE OE Laser '92, Conf. 1648, Jan. 92, 11 pages.

Green et al., "Burn Depth Estimation Using Indocyanine Green Fluorescence Arch Dermatol," vol. 128, Jan. 1992, pp. 43–49.

Moneta et al., "Infrared Fluorescence Videomicroscopy of Sking Capillaries With Indocynine Green," Int. J. Microcirc. Clin. Exp., pp. 25–34, (1987).

Gotti et al., "Evaluation of the Burn Wound with Perfusion Fluorometry," J. Trauma vol. 23, No. 3, Mar. 1983, pp. 202–206.

Afromowitz et al., "Multispectral Imaging of Burn Wounds," IEEE Trans. Biomed. Eng., vol. 35, No. 10, Oct. 1988, pp. 842–849.

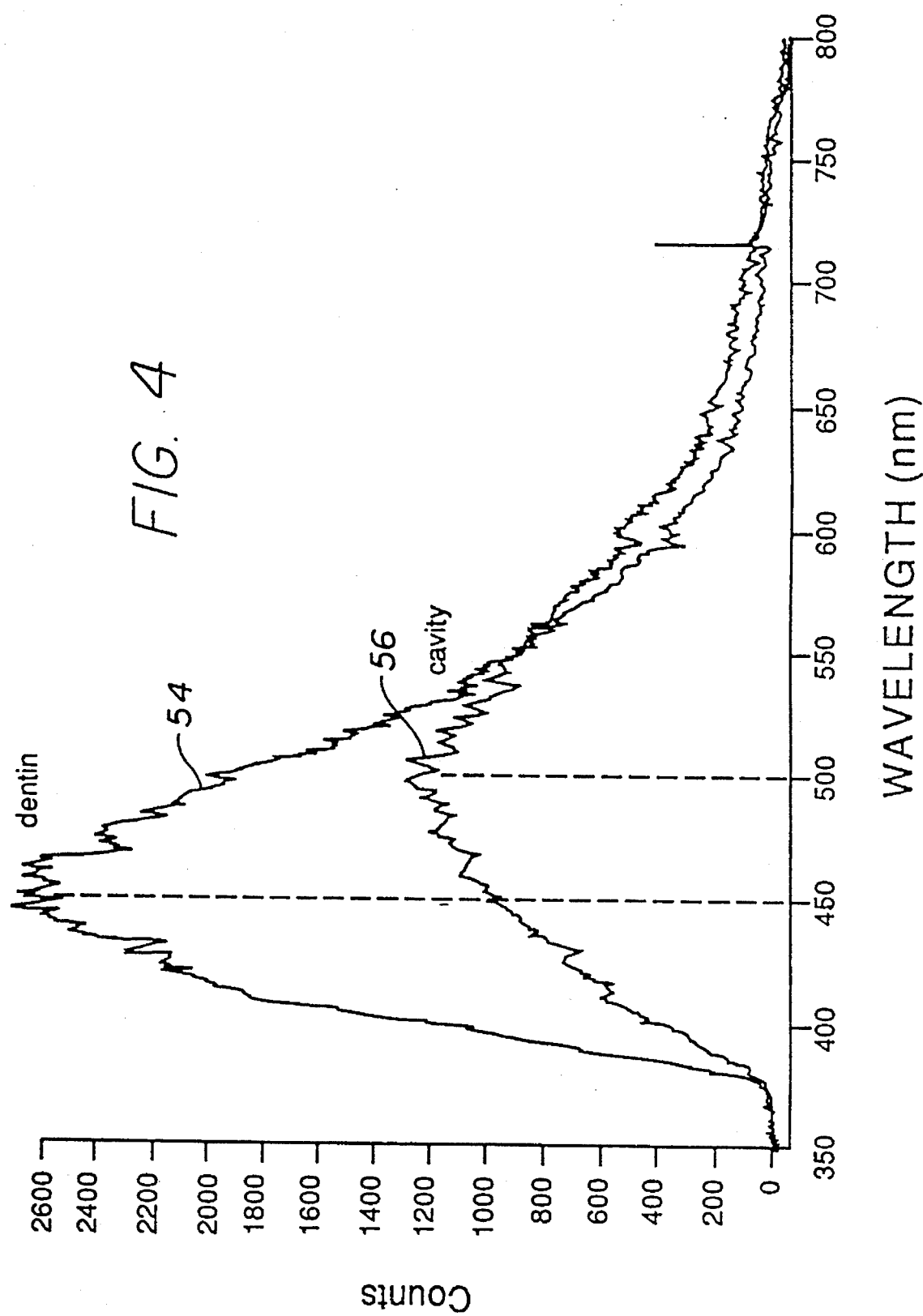

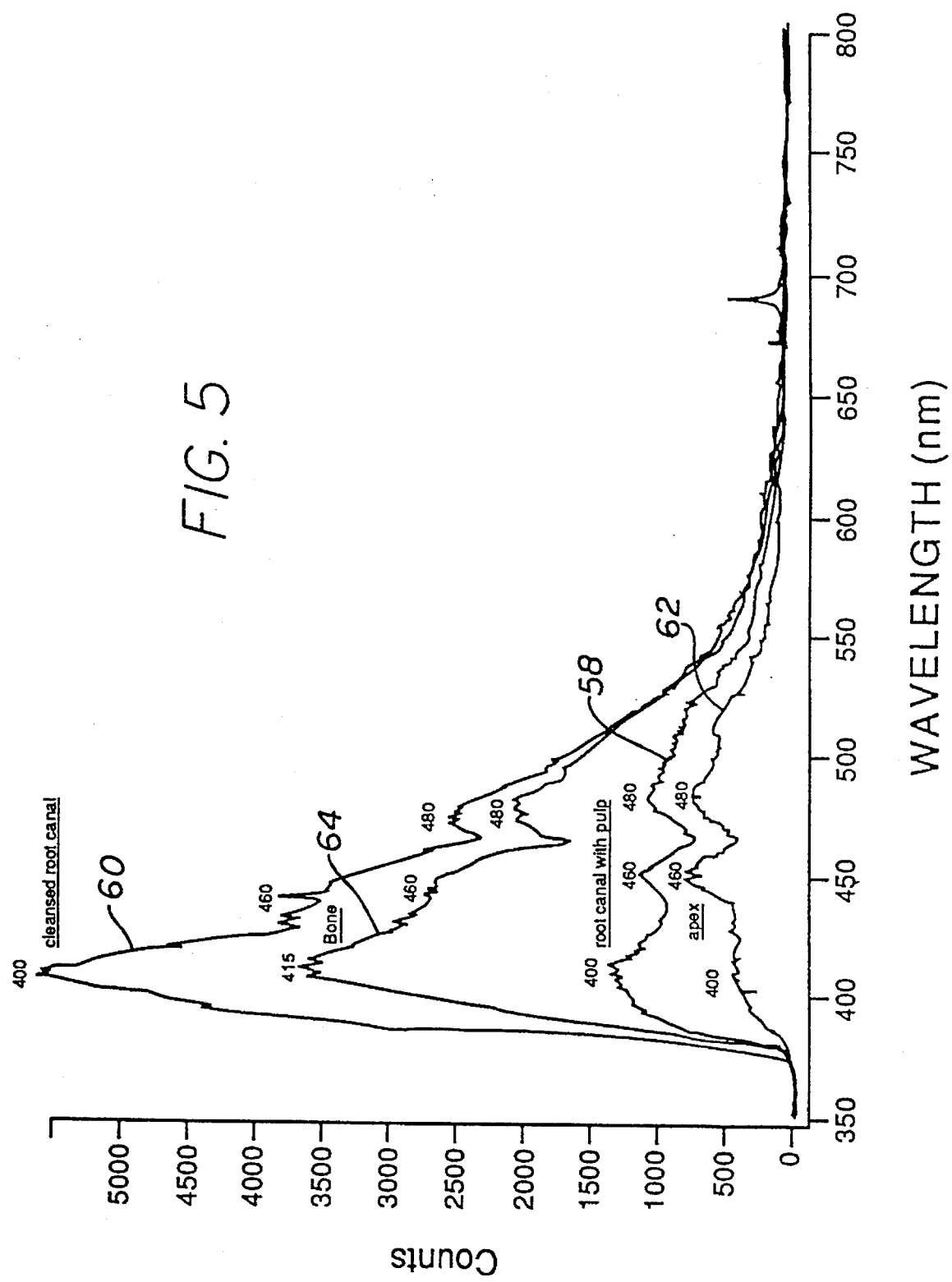

FIG. 11 ROOT CANAL WITH PULP

FIG. 12 ROOT CANAL AFTER CLEANSING

FIBER-OPTIC ENDODONTIC APPARATUS AND METHOD

BACKGROUND OF THE INVENTION

This invention relates generally to endodontic therapy and, more particularly, to the restoration of a dead or severely decayed tooth by preparing and filling the tooth's root canal with the assistance of optical techniques such as induced fluorescence spectroscopy.

The restoration of a dead or severely decayed tooth requires the tooth's root canal to be cleaned and sealed. The structure of a typical tooth 10 is shown in FIG. 1. The tooth has a crown 12 which extends above the gums 14 and is covered by enamel 16. At the heart of the tooth is the relatively soft living pulp 18 which includes blood vessels 20 and nerves 22. A hard substance called dentin 24 surrounds the pulp. The tooth also has one or more roots 26 below the gums that fit into sockets in the jawbone 28. Each root is covered by a sensitive, bone like material called the cementum 30. Within each root is a root canal 32. The root canal's structure may have dramatic curvatures and other complex microstructures at almost any position within the root. At the end or apex 34 of the root canal is a small opening, also called the apical foramen, through which the tooth's blood vessels and nerves enter into the root canal.

The ultimate success of the restoration of a tooth 10 is directly dependent upon the preparation of each root canal 32 and the integrity of the seal of the apex 34. Each root canal must be thoroughly cleaned eliminating tissue remnants, bacteria and antigenic inflammatory chemicals. Inadequate cleaning of the root canal may lead to short-term treatment failure, as well as long-term problems such as persistent inflammation and/or infection. Inadequate sealing of the apex 34 may allow contaminates to enter the root canal which may lead to persistent problems with or even failure of the tooth's restoration. The reintroduction of irritants and the slow dissemination of pathogenic substances through an unsealed opening exit is the most common cause of long-term endodontic failures.

Also, in conventional endodontic therapy, the root canal 32 must be shaped to allow controlled total filling of the root canal in all dimensions. Since a root canal frequently has an irregular structure, the shaping of the root canal must be carefully performed. As shown in FIGS. 2A and 2B, typical endodontic instruments, such as files 36 and the like, are much harder than the tooth's dentin 24 and tend to go in straight paths when used incorrectly. Such misuse of an endodontic file tends to cause blockages, ledges, via folsas 37, and perforations 38, all of which tend to decrease the chances of a successful tooth restoration. Also, incorrect use of a file may lead to overinstrumentation wherein too much healthy dentin is removed from the tooth which also tends to decrease the chances of a successful restoration.

As the root canal 32 is cleaned and shaped, the opening at the apex 34 of each root canal must be precisely located and prepared for sealing. The location and preparation of the opening greatly determines the effectiveness of the apical seal.

The proper preparation of the root canal 32 and location of the apex 34 typically requires a preoperative radiograph to gain insight into the size, shape and location of the root canal. However, the apical third of the root canal is obscured by the jawbone and tends to disappears from view on an x-ray image. The lack of a clear x-ray image of the apical third of the root canal adds to the uncertainty of the root canal's structure and the ultimate success of the restoration since this region of the root canal is where usually most of the root canals structural complexities are found. Certainly, more potential for irreversible damage exists in the apical third of a root canal than in the coronal two-thirds of the canal system. Other methods for determining the length of the tooth such as radiographs, tactile sense, and electronic apex detectors are not always able to precisely detect the location of the opening at the root canal's apex.

From the discussion above, it should be apparent that there is a need for a root canal explorer that can remove infected dentin with a minimum loss of healthy dentin, that can locate the opening at the root canal's apex, and that can seal the apex and fill the root canal while being relatively simple and rapid to use, and that provides lasting results. The present invention addresses these needs.

SUMMARY OF THE INVENTION

The present invention is embodied in an endodontic apparatus and related method for preparing, sealing and restoring a tooth's root canal using induced fluorescence spectroscopy. The apparatus accurately locates the root canal's apex, thus reducing the number of x-rays required and improving the likelihood of short-term and long-term success of the restoration.

The endodontic apparatus includes an elongated tool and an optical fiber. The elongated tool is sized to fit within the root canal and has a passage through its center through which the optical fiber passes. The optical fiber is retained in the passage and the tip of the optical fiber is exposed at the end of the tool which enters into the root canal.

In a more detailed feature of the invention, the optical fiber carries ultraviolet, visible (blue) or infrared light. Ultraviolet and blue light is used to induce fluorescence within the root canal and to active light cure epoxy. Infrared light is used to widen the canal and to remove blockages of root canal. As an additional feature the tool may include a stop slidably mounted on the outside surface of the tool to assist in determining the length of the root canal. Additionally, the tool's outside surface may have a slightly conical shape to better fit within the root canal. The conical surface may have metal flutes or sharpened edges for removing dentin from the root canal.

In another embodiment of the invention, the optical fiber of the endodontic tool is coupled to a light source, a sensor and a processor. The light source emits excitation light that is directed into the root canal by the optical fiber. The excitation light induces the tissues within the root canal to fluoresce. The fluorescence light is included with the return light that is captured by the optical fiber. The sensor monitors the return light and generates a plurality of electrical signals indicative of-the intensity of return light within predetermined wavelength bands. The processor processes the plurality of electrical signals to determine the structure and composition of the tissues within the root canal. The system can also determine whether a light cure restorative in the root canal has polymerized.

In a more detailed feature of the invention, the excitation light is narrowband light having a wavelength between 250 and 450 nanometers. The wavelength bands associated the plurality of electrical signals are within a wavelength range from about 50 nanometers to about 250 nanometers greater than the wavelength of the narrowband excitation light.

In another more detailed feature of the invention, the wavelength of the excitation is about 442 nanometers and the predetermined wavelength bands include two reference bands and a peak band. The first reference band extend from about 500 nanometers to about 520 nanometers. The second reference band extends from about 620 nanometers to about 640 nanometers. The peak band is centered about the intensity peak of the spectrum of the return light. The total width of the peak band is about 20 nanometers centered about the wavelength of the intensity peak.

A ratio may be calculated from values representing the intensity of light within the above-mentioned wavelength band. The ratio is calculated by subtracting the value associated with the second reference band from the value associated with the peak band and dividing the result by the value associated with the first reference band. The processor may also include an artificial neural network.

In a more detailed feature of the invention, the sensor may include an optical analyzer and a spectrograph having a detector array. Alternatively, the sensor may include a dichroic filter, a stop, a grating, and a plurality of optical detectors. The dichroic filter rejects any excitation that may be included in the return light. The stop has a slit for allowing only a narrow ribbon of light to reach the grating. The grating separates the return light along an axis at a distance proportional to the wavelength of the return light. A plurality of electro-optical detectors are located along the axis at predetermined locations.

In an alternative embodiment of the invention, the apparatus includes a plunger, a long hollow tube and an optical fiber. The plunger forces a light cure restorative through the tube to the apex of the root canal. Light is delivered through the optical fiber to activate and cure the light cure restorative, thus sealing the apex of the root canal. Similarly, the apparatus can be adapted to fill the sealed root canal with a light cure restorative.

Ideally, the entire root canal may be cleaned prepared and filled using the apparatus and method of the present invention. First, the crown of the tooth is opened and the pulp removed. Next, the entrance at the root canal is located using induced fluorescence spectroscopy. Then root canal is cleaned and shaped. Again, induced fluorescence spectroscopy is used to determine whether all the infected dentin has been removed, to determine the shape of the root canal, and to prevent damaging and perforating the root canal. Also, the apex is located using induced fluorescence spectroscopy and prepared. A light cure restorative is placed in the opening at the apex and activated with light. After the root canal is sealed, the remainder of the root canal is filled with light cure restorative.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 4 is a graph of the intensity of fluorescence verses wavelength of healthy and carious dentin in a human tooth excited by light having a wavelength of 308 nanometers.

FIG. 5 is a graph of the intensity of fluorescence verses wavelength of the bone, the apex, the root canal with pulp, apex and a diseased root canal of a rabbit tooth excited by light having a wavelength of 442 nanometers.

DESCRIPTION OF THE PREFERRED EMBODIMENTS

As shown in the exemplary drawings, the present invention is embodied in an endodontic system 40 for restoring a tooth by cleaning, sealing and filling a tooth's root canal with the assistance of induced fluorescence spectroscopy. The endodontic system 40 determines the structure of the tooth by monitoring the fluorescence of the tooth without the use of fluorescent dyes or the use of other indirect methods. Also, the fluorescence endodontic system tends to reduce the number of x-rays needed and to provide greater control in cleaning, shaping, sealing, and filling of the root canal. The fluorescence endodontic system further tends reduce the possibility of complications which may increase the chances of short-term or long-term failure of the restoration.

Figure 1:
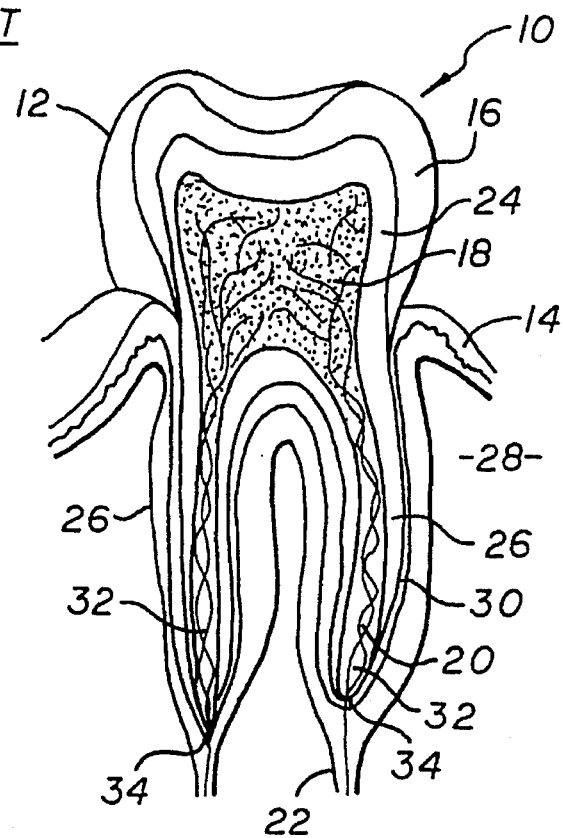
FIG. 1 illustrates the anatomy of a tooth.
Figure 2A:
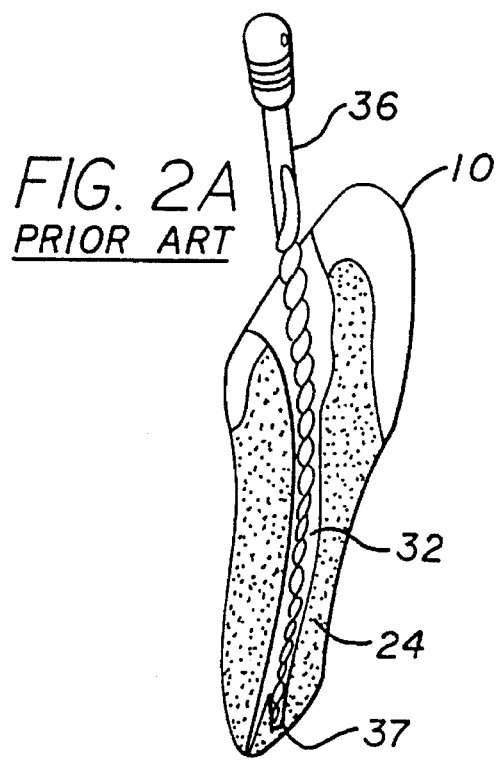
FIG. 2A illustrates a tooth having a via folsa created by an endodontic file.
Figure 2B:
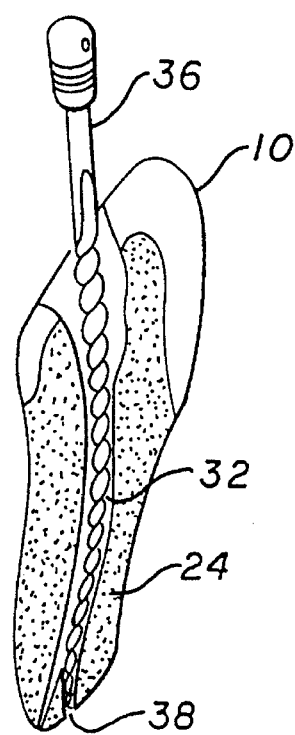
FIG. 2B illustrates a tooth having a perforated root caused by an endodontic file.
Figure 3:
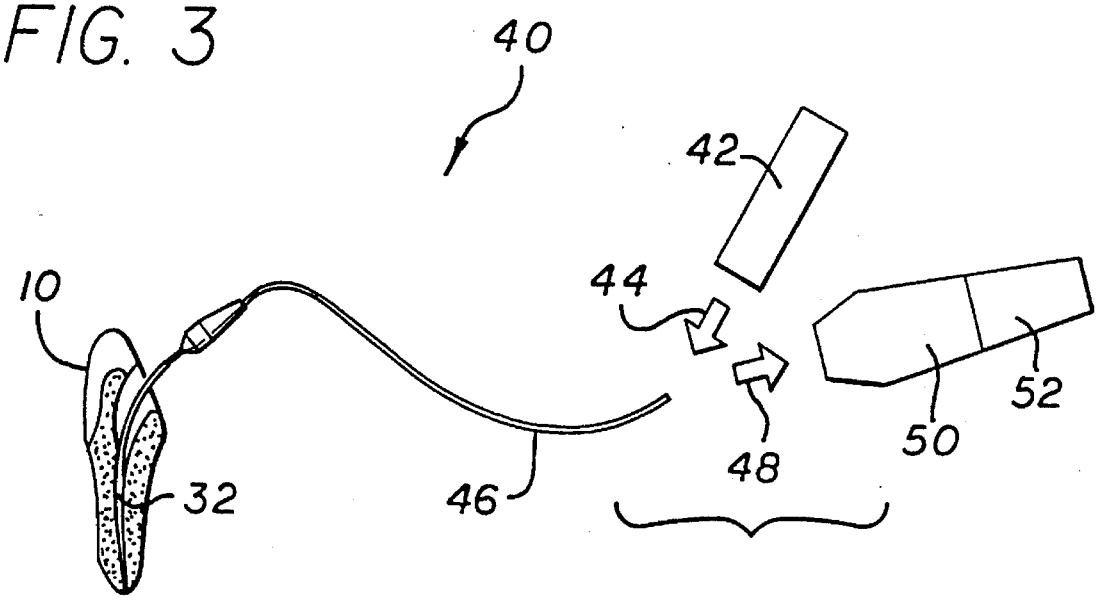
FIG. 3 is a block diagram of an induced fluorescence system of the present invention for determining the structure of a tooth's root canal.

In the system 40, shown in FIG. 3, a light source 42 directs ultraviolet or blue excitation light 44 into a tooth's root canal 32 through an optical fiber 46 to illuminate and induce the tissues within the tooth 10 to fluoresce. The optical fiber collects return light 48 from the illuminated tissues within the tooth, such return light including the tissue's fluorescence light and scattered excitation light. A sensor 50 monitors the return light collected by the optical fiber and generates electrical signals corresponding to the intensity of return light within predetermined wavelength bands. The electrical signals represent the intensity of return light within spectral wavelength bands corresponding to wavelength characteristics of the fluorescence of the various tissues. The electrical signals are communicated from the sensor to a processor 52. The processor then processes the electrical signals to determine the composition and the structure of the tissues within the root canal.

The light source 42 is also referred to as the excitation source. The excitation light 44 from the light source typically has a wavelength between 250 nanometers and 450 nanometers. The excitation light can be produced from any type of ultraviolet or blue light source. In the preferred embodiment, the light source is an excimer (XeCl) laser producing narrow-band ultraviolet light having a wavelength of about 308 nanometers or a helium-cadmium (HeCd) laser producing narrow-band blue light having a wavelength of about 442 nanometers. Alternatively, a nitrogen laser, a frequency-multiplied diode laser, a solid-state laser, arc lamp or light emitting diode (LED) can be used. The output power of the light source is typically 200 microwatts to 5 milliwatts. Higher or lower output power levels can be used depending upon the equipment and wavelength used. However, care must be taken to ensure that the energy density is not too high or too low. If the energy density is too high, ablation of the sample may occur, whereas if the energy density is too low, obtaining a sufficient electrical signal may be difficult.

The detectors in the sensor 50 can be as simple as individual light-sensitive diodes, with appropriate bandpass filters, or more complicated such as a optical spectrum analyzer that analyzes a broad spectrum of the return light. Preferably, the sensor is a suitable optical spectrometer having an array detector used to monitor a variety of wavelengths and produce corresponding electrical signals. A suitable optical spectrometer is a SPEX 500M available from SPEX Industries, Inc. of Edison, N.J. A suitable array detector is a Model 1420 or 1421 intensified silicon photodiode array detector available from EG&G Princeton Applied Research of Princeton, N.J.

In its simplest form, the processor 52 receives the electrical signals from the sensor 50 and algebraically manipulates or combines the signals to determine and indicate the composition of the tissue in the root canal 32 in a well understood manner.

The process of determining the structure and composition in the root canal is better understood with reference to FIG. 4. The two spectral signals shown in FIG. 4 are the fluorescence spectrum of healthy and diseased portions of a human tooth after excitation with an ultraviolet excimer laser light having a wavelength of 308 nanometers. Each spectrum has a different peak wavelength. The spectrum for healthy dentin 54 has a peak centered at approximately 450 nanometers, and the spectrum for infected dentin 56 has a peak centered at approximately 500 nanometers. Thus, the wavelength of the peak corresponding to the healthy dentin fluorescence is approximately 50 nanometers shorter than the wavelength of the peak corresponding to the infected dentin's fluorescence. This wavelength difference is used to determine whether the infected dentin has been sufficiently removed from the root canal.

Referring now to FIG. 5, the fluorescence spectrum is shown for the different tissues or components of the root canal 32 of a rabbit tooth after excitation with an ultraviolet excimer laser light having a wavelength of 308 nanometers. The fluorescence spectrum of the root canal with pulp 58 is shown having a main peak at 400 nanometers and minor peaks at 460 and 480 nanometers. The fluorescence spectrum of the cleansed root canal 60 is shown as having similar peaks of different height ratios. The fluorescence spectrum of the apex of the root canal 62 is shown having two main peaks at 460 and 480 nanometers and a minor peak at 400 nanometers. The fluorescence spectrum of the bone of the jawbone 64 is shown to have a main peak at 415 nanometers and minor peaks at 460 and 480 nanometers. As will be discussed further, this graph illustrates that the different spectral profile of the different components of the tooth can be used to determine the structure and composition of the tooth.

Figure 6:
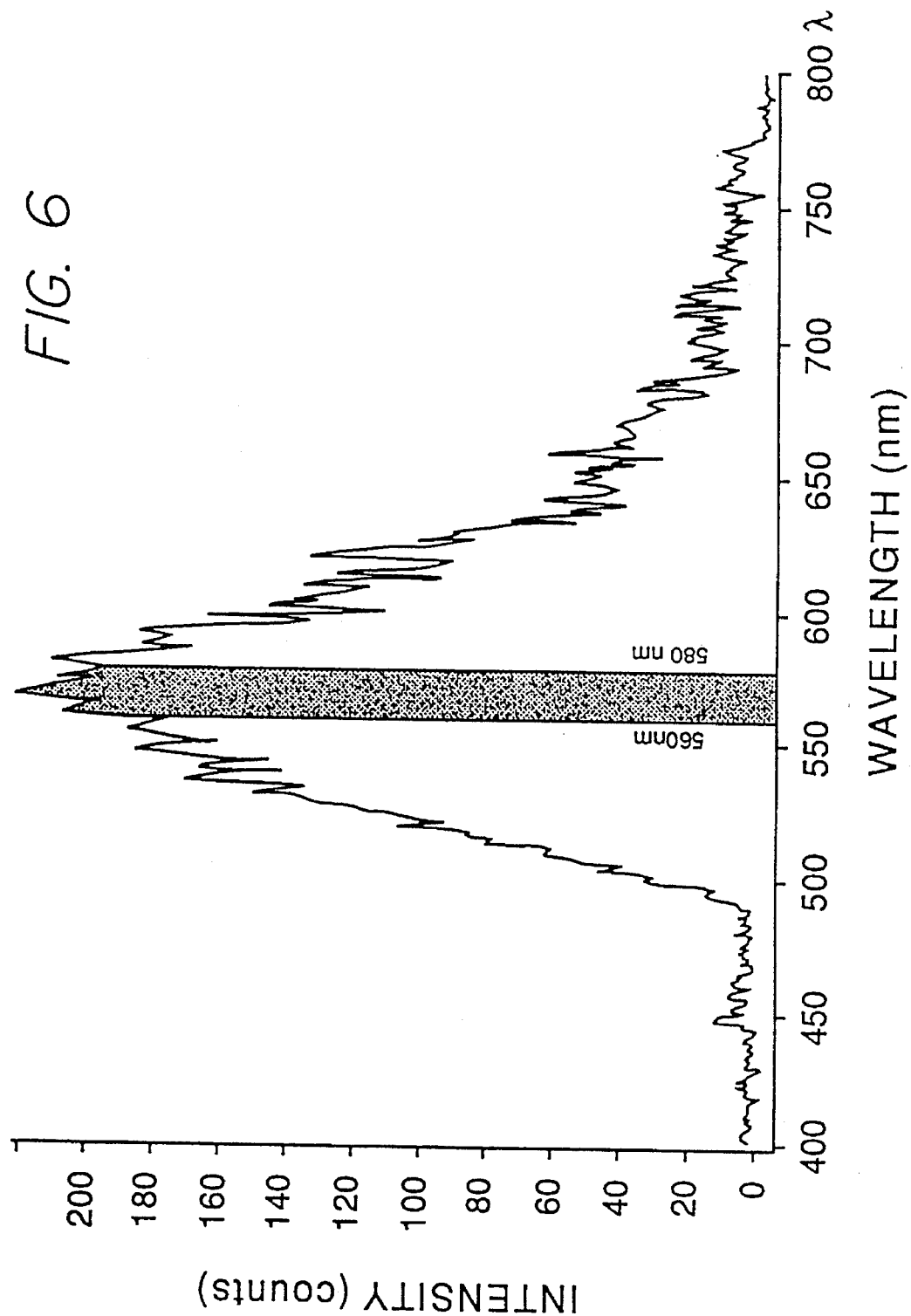
FIG. 6 is a graph of the intensity of fluorescence verses wavelength of the enamel of a porcine tooth excited by light having a wavelength of 442 nanometers.
Figure 7:
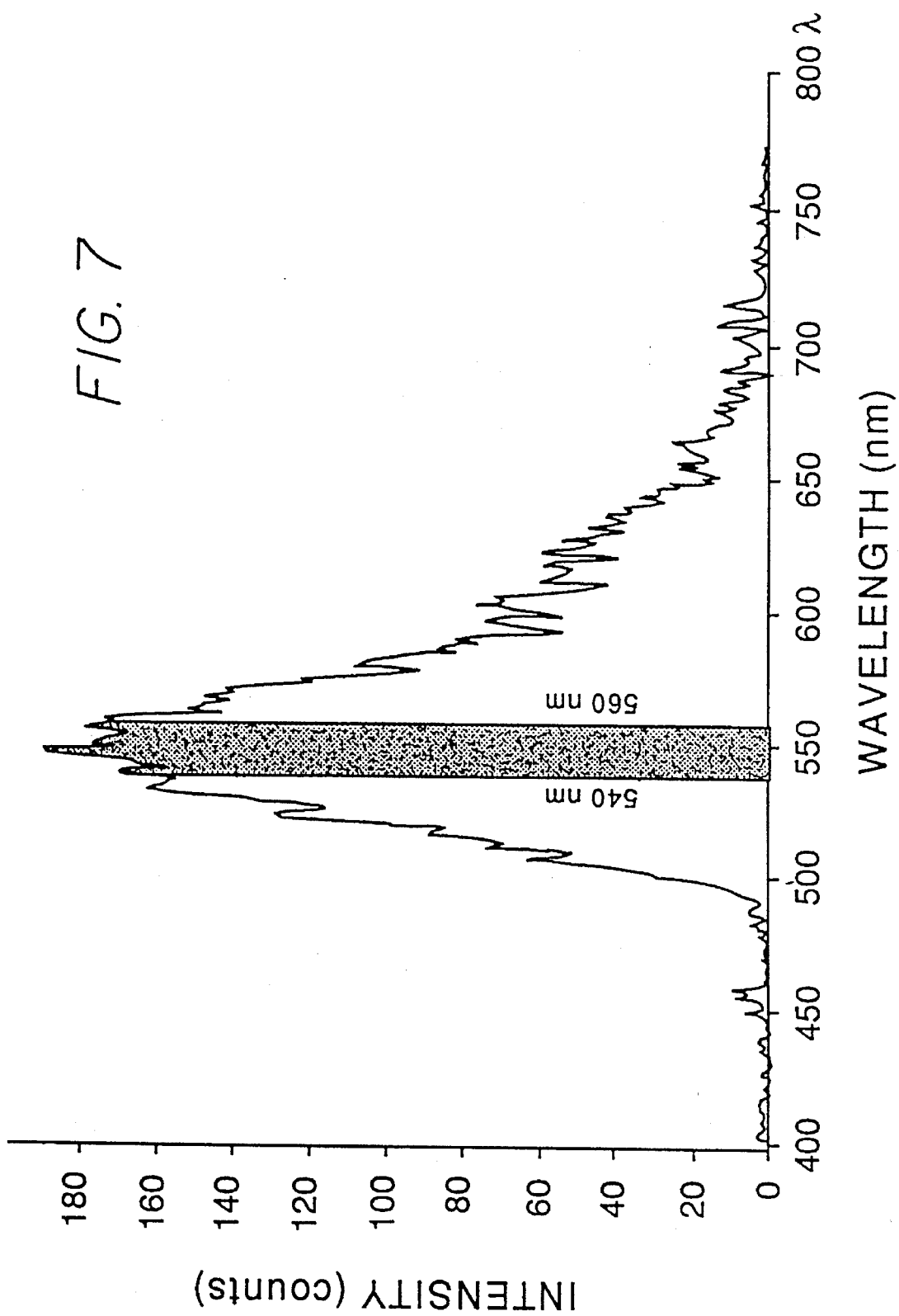
FIG. 7 is a graph of the intensity of fluorescence verses wavelength of the dentin of a porcine tooth excited by light having a wavelength of 442 nanometers.
Figure 8:
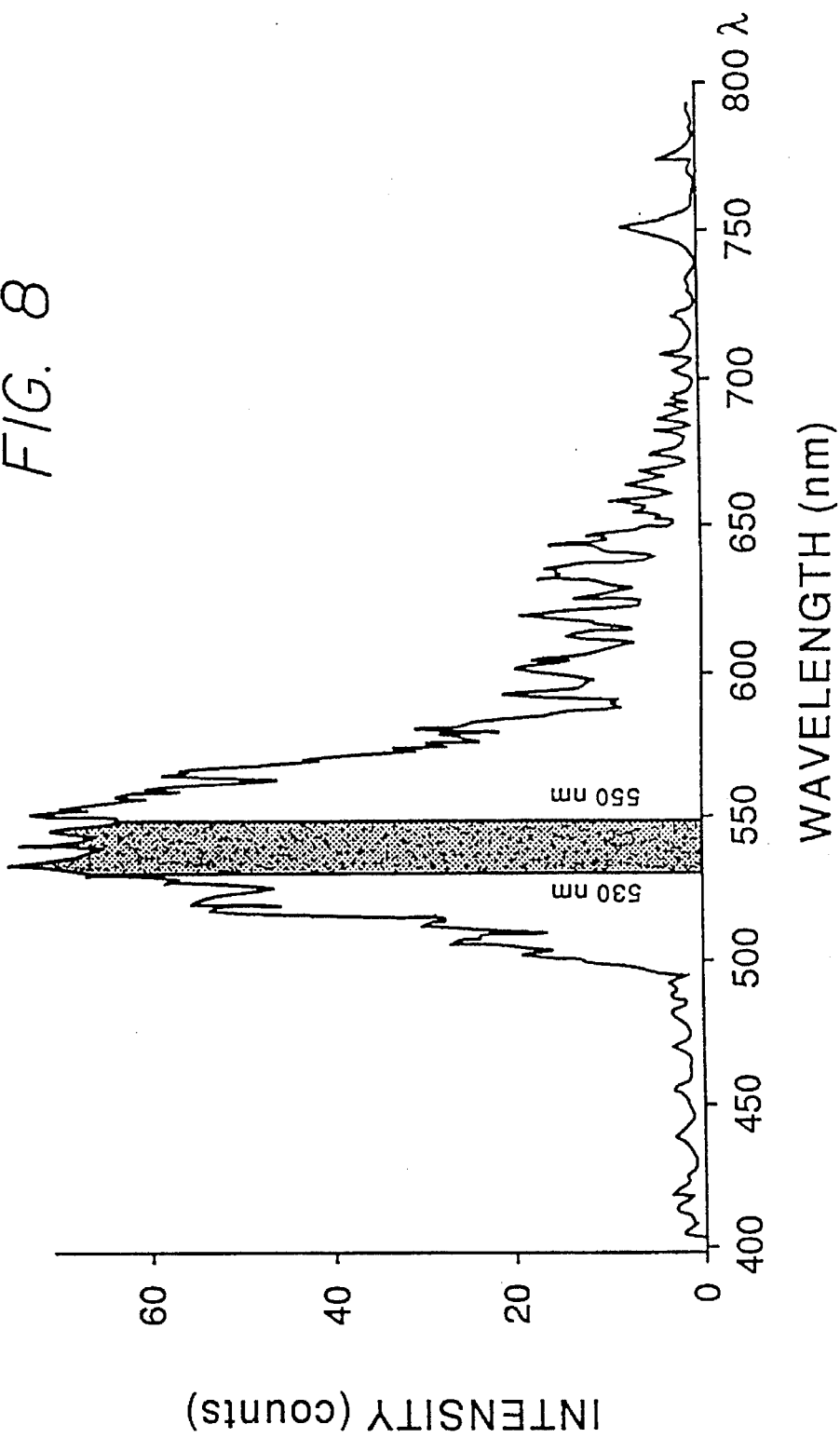
FIG. 8 is a graph of the intensity of fluorescence verses wavelength of the cementum of a porcine tooth excited by light having a wavelength of 442 nanometers.
Figure 9:
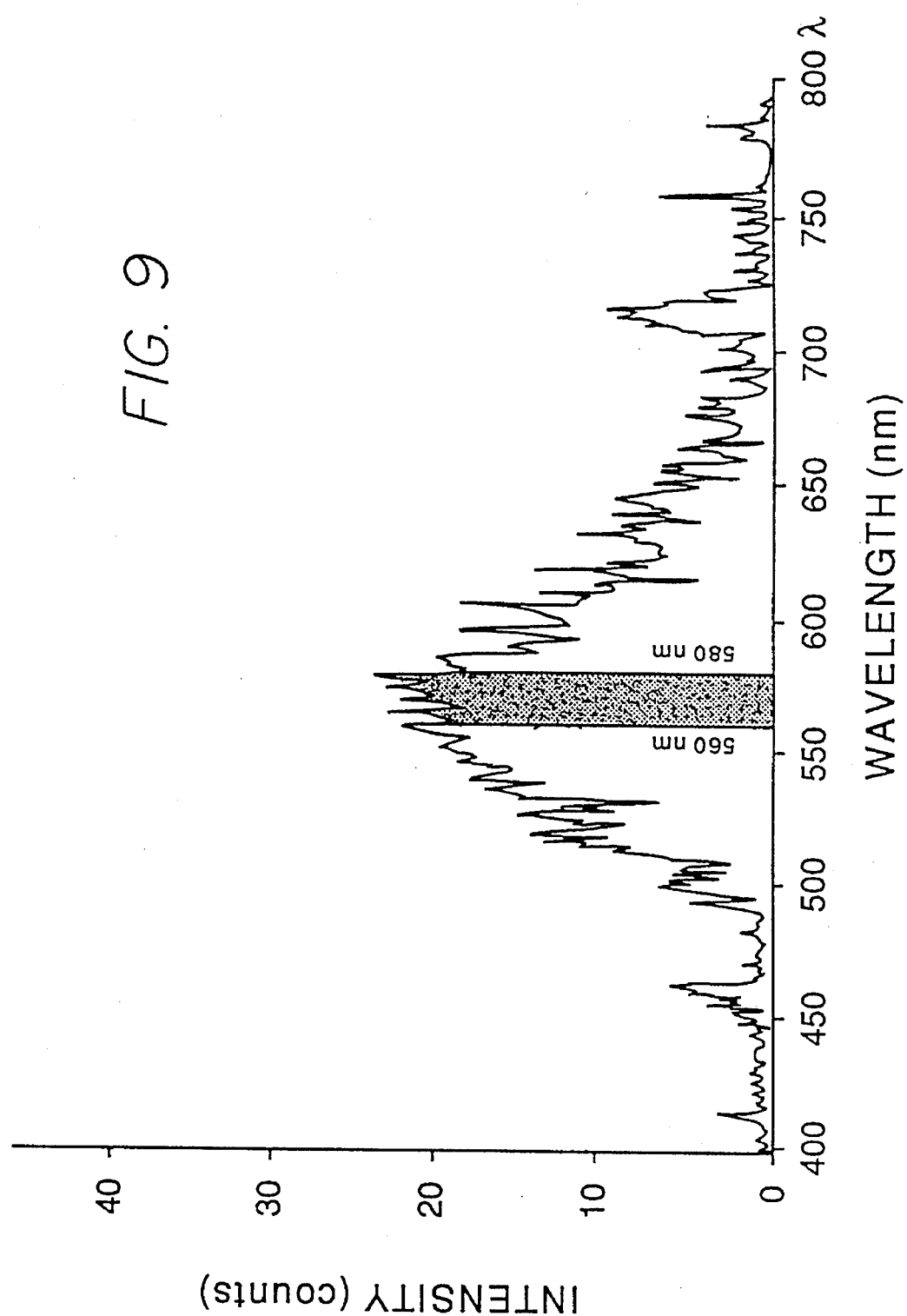
FIG. 9 is a graph of the intensity of fluorescence verses wavelength of the jawbone surrounding a porcine tooth excited by light having a wavelength of 442 nanometers.
Figure 10:
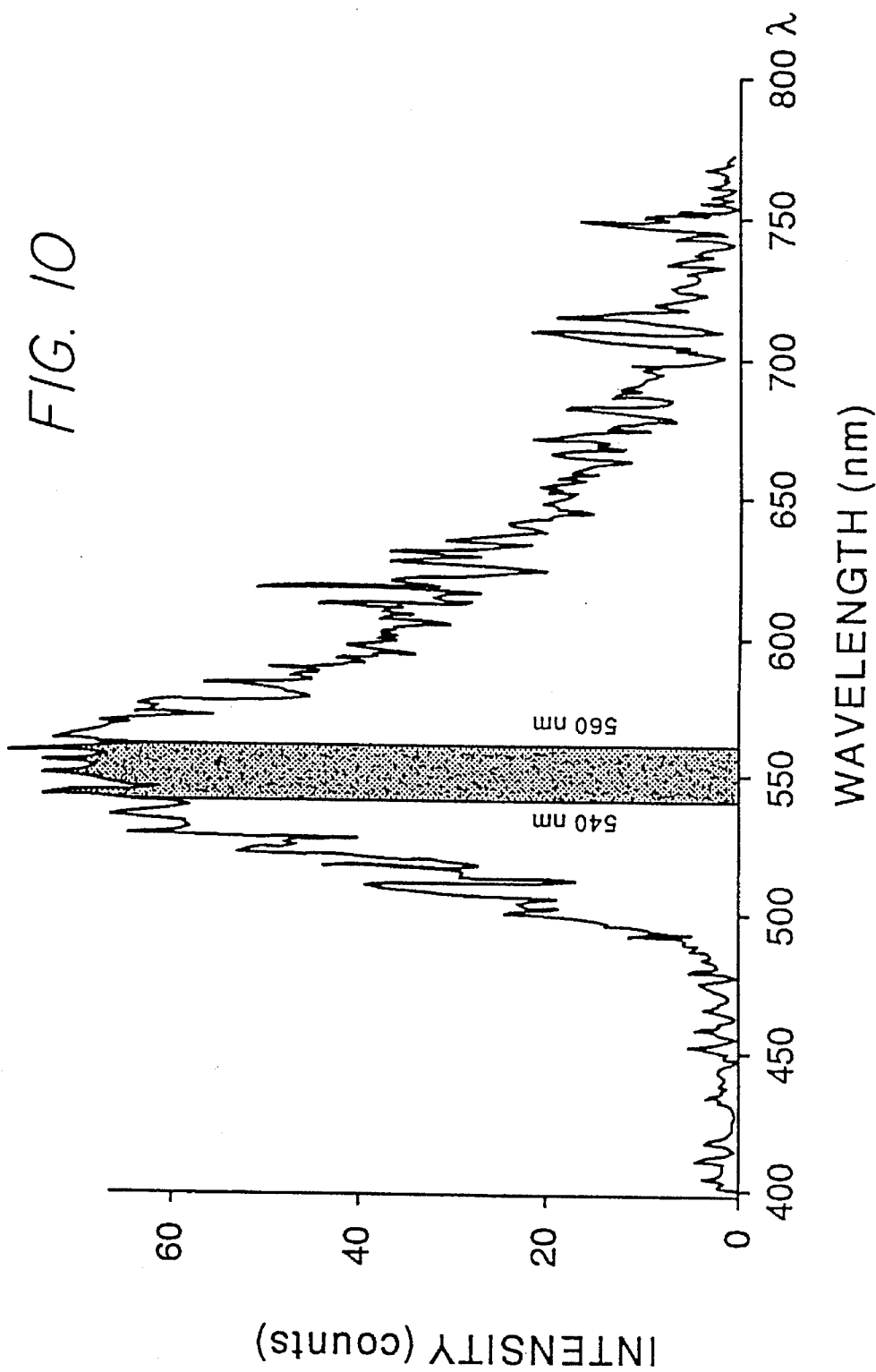
FIG. 10 is a graph of the intensity of fluorescence versus wavelength of the pulp of a porcine tooth excited by light having a wavelength of 442 nanometers.
Figure 11:
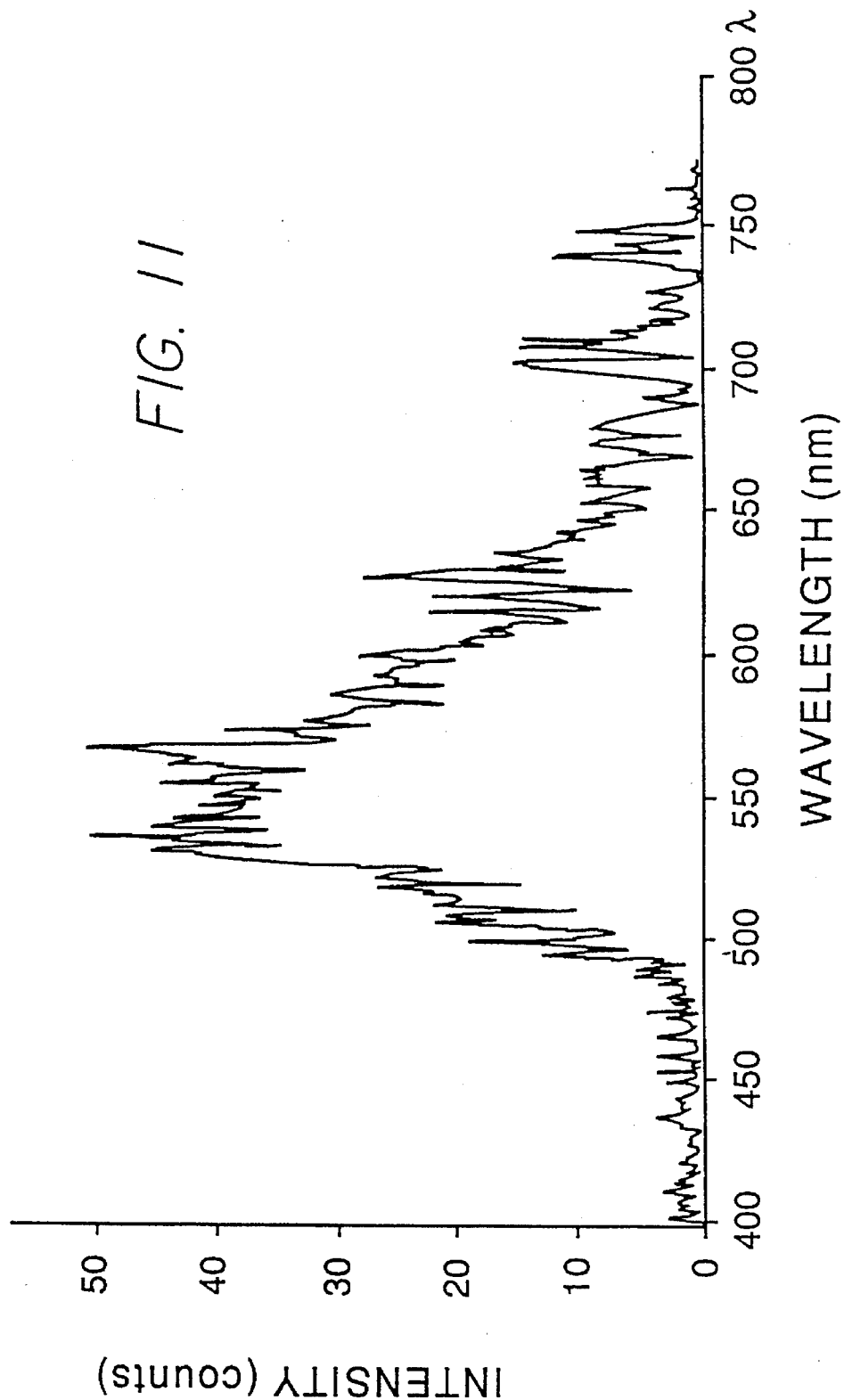
FIG. 11 is a graph of the intensity of fluorescence verses wavelength of the root canal with pulp of a porcine tooth excited by light having a wavelength of 442 nanometers.
Figure 12:
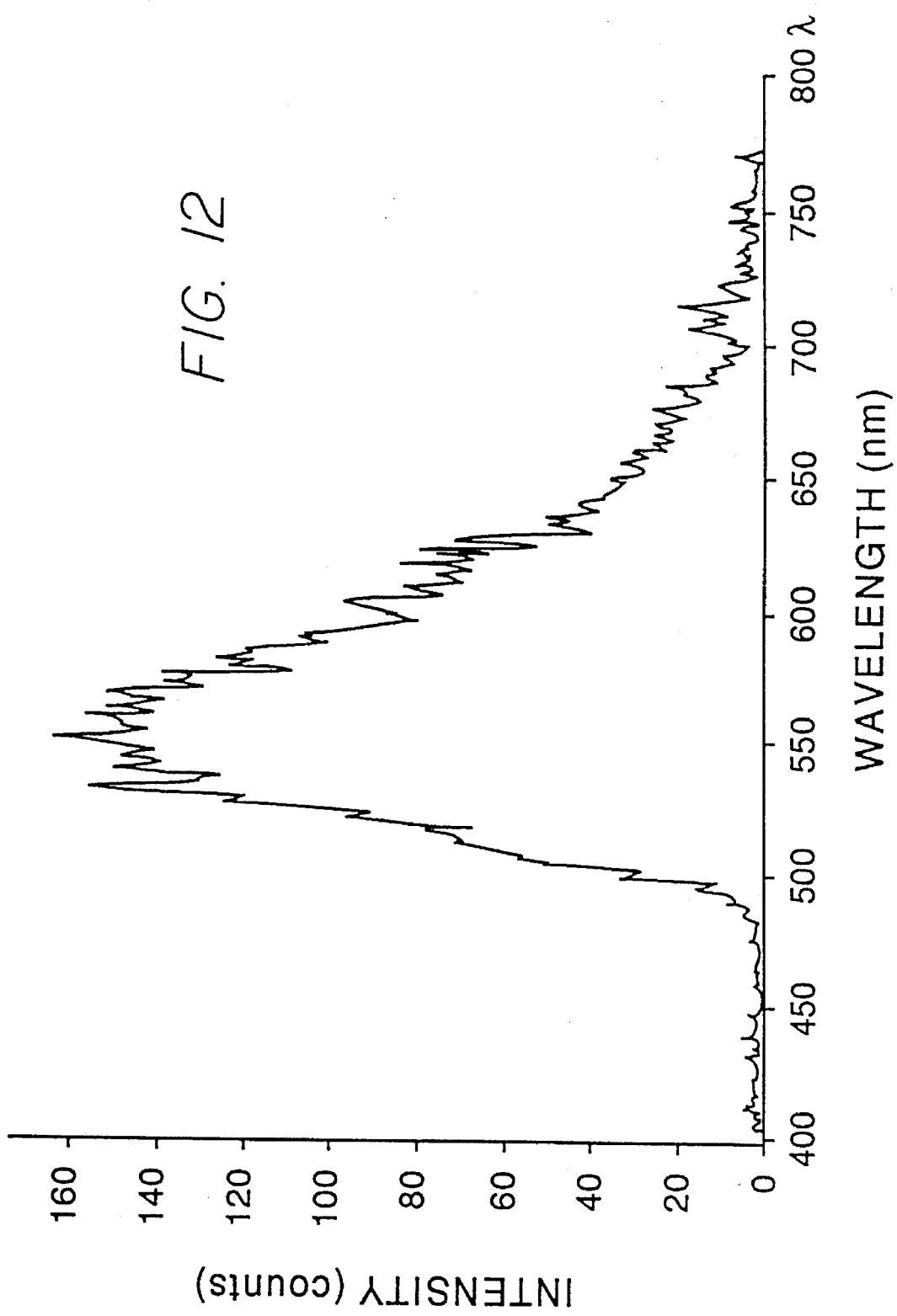
FIG. 12 is a graph of the intensity of fluorescence versus wavelength of the root canal after cleaning of a porcine tooth excited by light having a wavelength of 442 nanometers.
Figure 13:
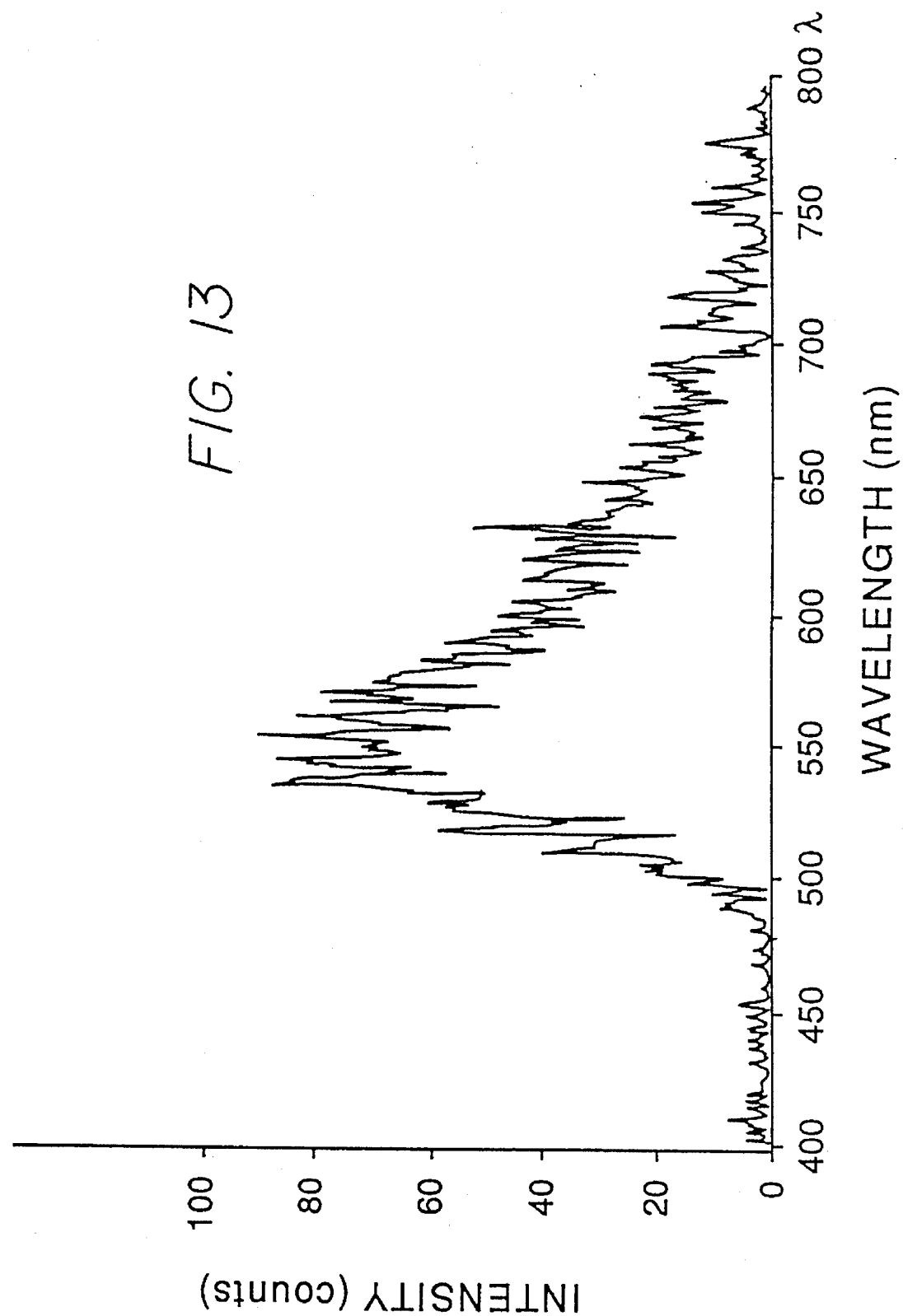
FIG. 13 is a graph of the intensity of fluorescence versus wavelength of the apex of the tooth of a porcine tooth excited by light having a wavelength of 442 nanometers.

Referring now to the graphs in FIGS. 6–13, the fluorescence spectrum is shown in these graphs for the different tissues or components of the root canal of a porcine tooth after excitation with light having a wavelength of 442 nanometers produced by a suitable HeCd laser. As shown in FIG. 6, the fluorescence spectrum of the enamel of the porcine tooth has a peak between 560 and 580 nanometers. As shown in FIG. 7, the fluorescence spectrum of the dentin of a porcine tooth has a peak between 540 and 560 nanometers. As shown in FIG. 8, the fluorescence spectrum of the cementum of a porcine tooth has a peak between 530 and 550 nanometers. As shown in FIG. 9, the fluorescence spectrum of the jawbone supporting a porcine tooth has a peak between 560 and 580 nanometers. As shown in FIG. 10, the fluorescence spectrum of the pulp of a porcine tooth has a peak between 540 and 560 nanometers. As shown in FIGS. 11, the root canal with pulp of a porcine tooth has a fluorescence spectral profile distinct from the fluorescence spectral profile shown in FIG. 12 of the root canal after cleansing. As shown in FIG. 13, the apex of the root canal of a porcine tooth has a fluorescence spectral profile distinct from that of the cleansed root canal.

By monitoring the intensity of the fluorescence spectrum within several wavelength bands and comparing that intensity with reference wavelength bands, the composition of the porcine tooth may be determined. The following formula provides a ratio that identifies the composition of the tooth:

$$\text{RATIO} = (S^{Peak} - S^{Ref\ Long})/(S^{Ref\ short})$$

where $S^{Peak}$ is the intensity of light within the peak wavelength bands of 20 nanometers discussed above, $S^{Ref\ Long}$ is the intensity of light within a reference wavelength band at wavelengths that are longer than the peak wavelength and $S^{Ref\ Short}$ is the intensity of light within a reference wavelength band at wavelengths shorter that are shorter than the peak wavelength. The two reference bands are chosen to cover the tail at each end of the emission band of the fluorescence spectrum. Since the wavelength profile of a given fluorescence spectrum shifts in relation to a shift in the excitation light's wavelength, the reference band is chosen in view of the wavelength of the excitation light.

For the fluorescence spectrum shown in FIGS. 6–13, the reference band $S^{Ref\ Long}$ is between 620 and 640 nanometers and the reference band $S^{Ref\ Short}$ is between 500 and 520 nanometers. Thus, the following formula provides a ratio that identifies the composition of the tooth when excitation light having a wavelength of 442 nanometers is used:

$$RATIO=(S^{Peak}-S^{620-640})/(S^{500-520})$$

where $S^{620-640}$ is the intensity of light within a reference wavelength band between 620 and 640 nanometers and $S^{500-520}$ is the intensity of light within a reference wavelength band between 500 and 520 nanometers.

The results of this calculation applied to spectral profiles obtained from experimental measurements performed on several porcine teeth are summarized in the following table:

| Components | Ratios |
| --- | --- |
| Enamel | 1.923 ± 0.683 |
| Dentin | 1.806 ± 0.306 |
| Cementum | 2.048 ± 0.572 |
| Pulp | 1.426 ± 0.318 |
| Structures | Ratios |
| Root canal with pulp | 1.321 ± 0.410 |
| Root canal = cleansed | 1.524 ± 0.361 |
| Apex of the tooth | 1.359 ± 0.165 |
| Jawbone | 1.202 ± 0.312 |

By knowing the wavelength of the peak fluorescence band and the ratio calculated as discussed above, the composition within the root canal is determined.

Figure 14:
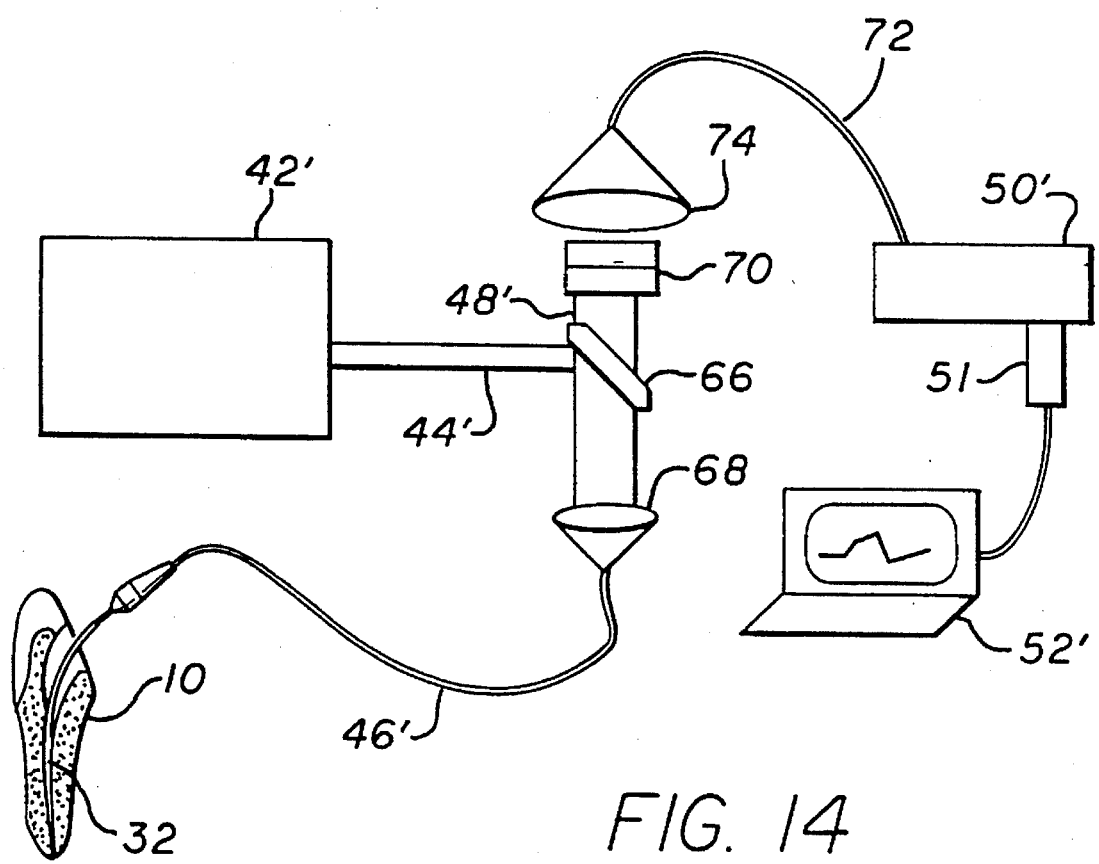
FIG. 14 is a block diagram of one embodiment of the induced fluorescence system shown in FIG. 3.

FIG. 14 shows an additional embodiment of the present invention, for determining the composition and anatomical boundaries of the root canal 32 of a tooth 10. The light source 42', a suitable HeCd low power laser, directs the excitation light 44' having a wavelength of 442 nanometers towards a suitable dichroic mirror 66. The dichroic mirror, preferably but not necessarily one supplied by CVI of New Mexico, exhibits high reflectance at 442 nanometers and high transmittance at 500 nanometers. The dichroic mirror reflects the excitation light towards a first lens 68.

The first lens 68 focuses the excitation light 44' into the end of an optical fiber 46' and also collimates the collected return light 48' that is emitted from the optical fiber. The optical fiber has a 400 micrometer core diameter. The distal end of the optical fiber scans the root canal 32 by directing the excitation light in the root canal. The same distal end also collects the return light 48' from the root canal. The return light passes from the fiber through the first lens, the ultraviolet mirror 66 and a long pass optical filter 70. The long pass optical filter has a cutoff wavelength of 325–345 nanometers to filter scattered or reflected excitation light from the return light. The fluorescent light is focused into a second optical fiber 72 by a second lens 74. The second optical fiber transmits the return light to the entrance of a spectrograph 50'. At the entrance of the spectrograph is a suitable long pass filter, such as the Schott GG475 filter, which further excludes any reflected excitation light from the return light. After the filter is a slit having a slit width of 50 micrometers. The slit is followed by a diffraction grating having 100 grates per millimeter that resolves the return light along an axis.

Along the axis is positioned a detector 51, preferably a 1024 element linear device array detector (EG&G 1422G). Each element of the detector array corresponds to a spectral wavelength band of the return light. The detector array provides an analog signal that is converted into a digital signal for analysis and processing by an optical multichannel analyzer 52'. The digital signal contains data representing the intensity of light received for each of the spectral wavelengths. The data may also be displayed on the screen of the optical-multi-channel analyzer 52' or saved on a data disk. A suitable system which includes both a detector and a multichannel analyzer is an OMA®4 available from EG&G Princeton Applied Research of Princeton, N.J.

The ratio of the light intensity collected in the several spectral wavelength bands or regions is calculated as discussed above. Using the calculated ratio, the intensity of light within a peak wavelength band is analyzed with the intensity of light with other spectral wavelength bands to identify the portion of the tooth within the root canal thus determining the anatomical boundaries of the tooth.

In an alternative embodiment of the present invention, the sensor 50 may include an aberration corrected wavelength division multiplexer (WDM) and a 512×512 pixel charged-coupled device (CCD) array. The fiber 46 which transmits and couples the return light into an f/2, 15 centimeter focal length aberration corrected WDM and the 512×512 pixel CCD array. The WDM's grating will be set at a fixed angle covering a 350 nanometer (300–650 nanometers) spectral range. The light exposure (light intensity×exposure time) for each pixel is digitized on a linear scale from 0 to $2^{14}$(16, 384). The array may be liquid nitrogen cooled array which results in a substantial reduction of background noise signals. In addition, since the background noise signals are almost uniformly distributed across the array, the average noise signal may be subtracted from the fluorescence signal from each detector element of the array. A suitable sensor is the 1530-CUV cryogenically cooled CCD detector available from EG&G Princeton Applied Research of Princeton, N.J.

In another alternative embodiment, the sensor 50 may include a photodetector (PD) array having a built-in thermoelectric cooler (TEC). The TEC cooled array detector operates with lower noise levels than room temperature array detectors. A suitable TEC cooled array is the 1530-PUV thermoelectrically cooled CCD detector available from EG&G Princeton Applied Research of Princeton, N.J.

Figure 26:
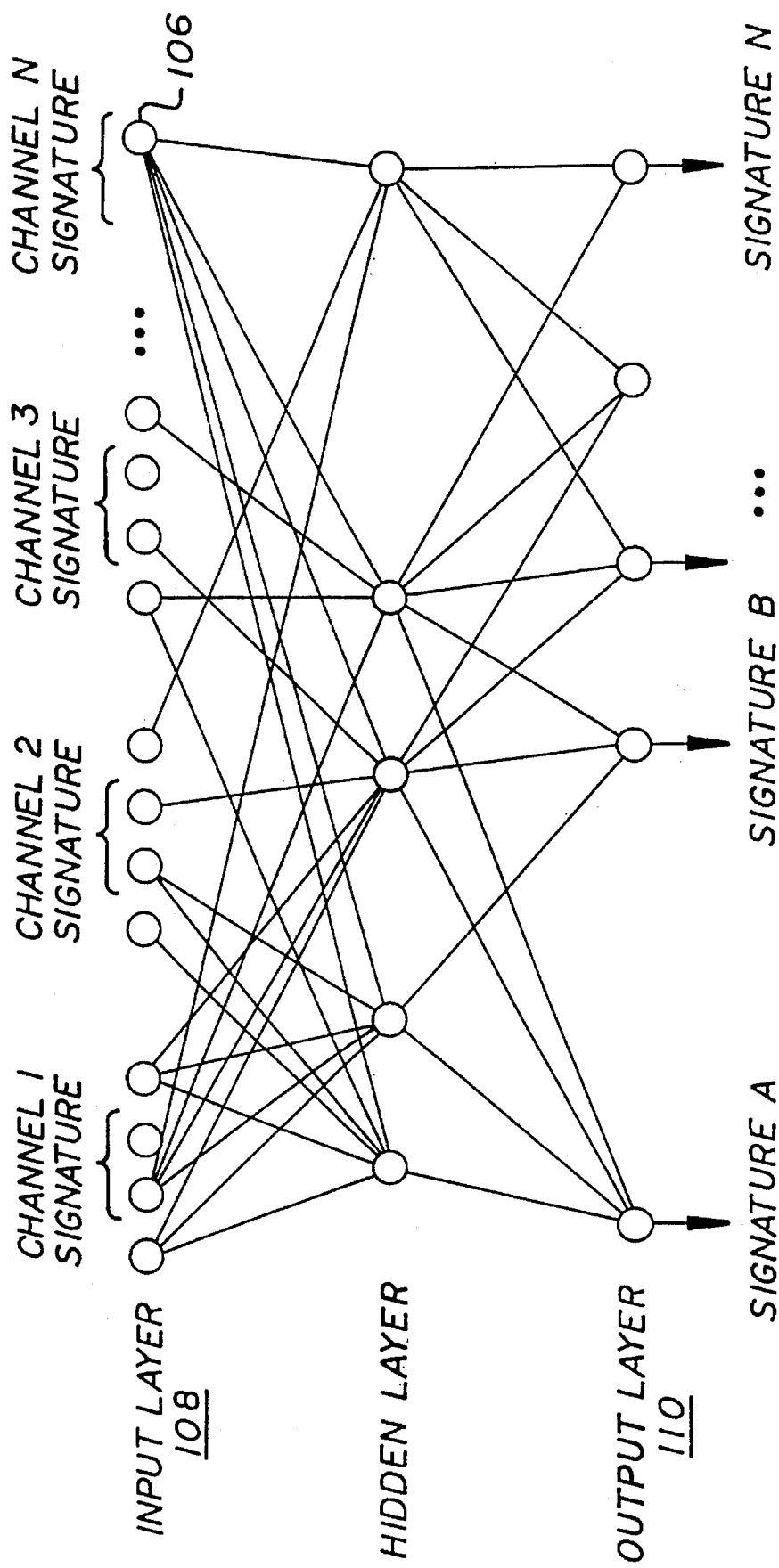
FIG. 26 is a schematic diagram of the concept of a neural network.

In an alternative embodiment of the invention, the processor 52' may include an artificial neural network as shown in FIG. 26. The artificial neural network consists of layers of interconnected processors (neurons) 106. The spectral data from the sensor 50' is input at the input neuron layer 108. Preferably, each of the wavelength bands discussed is divided into 10 smaller bands or windows. The input neuron layer has sufficient inputs to receive the data for each wavelength band of interest. The neural network performs a nonlinear transformation on the input data and produces its result at the output neuron layer 110. Neural network has great flexibility in that it can be taught to transform the spectral data (input neuron layer) into an output (output neuron layer) that automatically and uniquely identifies the components of the tooth with relatively very high sensitivity (one to two orders higher than the conventional detection limit), high speed (a fraction of a second for identifying one spectrum), and high reliability (confidence level being indicated by neural network output). The software implementing the neuron network is preferably the substance identification "Neural Network" software package from Physical Optics Corporation of Torrance, Calif. The neural network operations and decision making may be performed on an IBM compatible personal computer.

Figure 15:
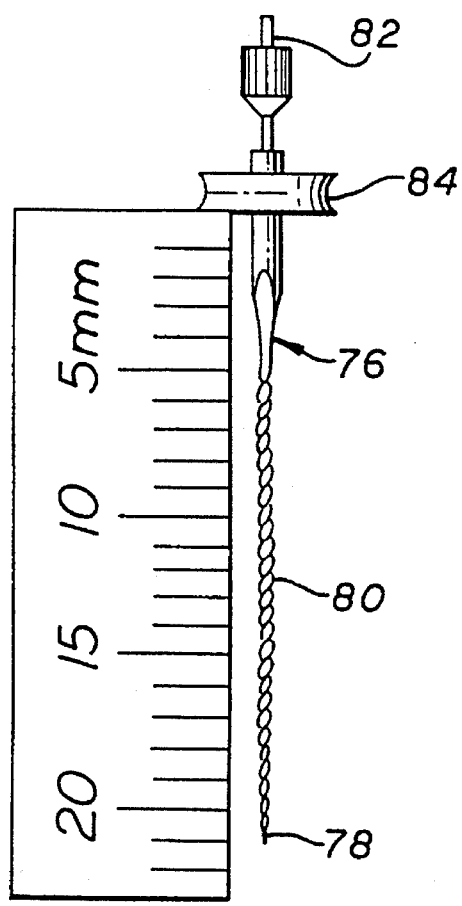
FIG. 15 illustrates one embodiment of an endodontic apparatus of the present invention called a fiber-optic reamer.

Referring now to FIGS. 15–21, endodontic tools embodying the present invention using induced fluorescence spectroscopy are used to shape, clean, and prepare a root canal 32. A fiber-optic reamer 76 is shown in FIG. 15. The fiber-optic reamer includes a metal-coated optical fiber 78 through its center. To manufacture the fiber-optic reamer, sections of round-tapered metal stock having a passage through its center are machined into triangular shaped blades. The machined blades are then twisted to produce the flutes 80. The optical fiber, preferably a metal-coated optical fiber, is retained or otherwise secured in the passage. The reamer shaves dentin when the sharp blades are rotated clockwise in the canal. The optical fiber is exposed at the tip of the fiber-optic reamer such that the optical fiber can transmit the excitation light into the canal and can collect and transmit the return light from the canal. The optical fiber can also transmit infrared (IR) light to ablate tissue and obstructions. The fiber can also transmit ultraviolet light to kill bacteria in the root canal. At the other end of the fiber is a fiber-optic connector 82. Optimally, a stop 84 may be included on the upper portion of the file for use by those dentists comfortable with the current practice of using a stop to determine the length of the root canal.

Figure 16:
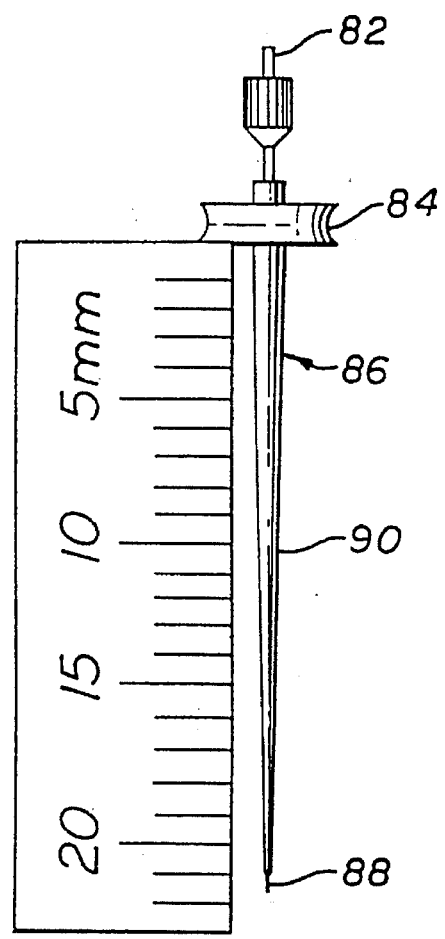
FIG. 16 illustrates another embodiment of the endodontic apparatus of the present invention called a fiber-optic root canal file.

A fiber-optic file 86 of the present invention is shown in FIG. 16. The fiber-optic file includes an optical fiber 88 through its center. Generally, the blade 90 is ground into a square tapered blank. The file acts by scrapping dentin from the walls of the canal in a rasping action. A reaming action also can be accomplished by slightly rotating the instrument. The fiber-optic file has the optical fiber exposed at the tip of the file. As discussed with respect to the fiber-optic reamer, the fiber can transmit IR, visible and UV light into the root canal and transmit return light from the root canal. Stop 84 also may be included.

Figure 17:
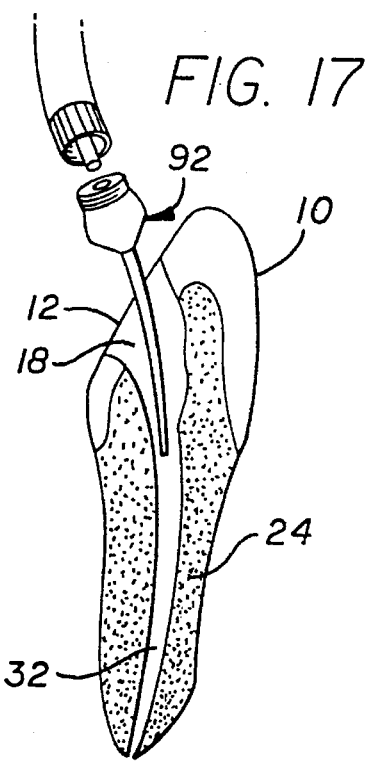
FIG. 17 illustrates another embodiment of the endodontic apparatus of the present invention called a fiber-optic root canal explorer for locating the root canal.
Figure 18:
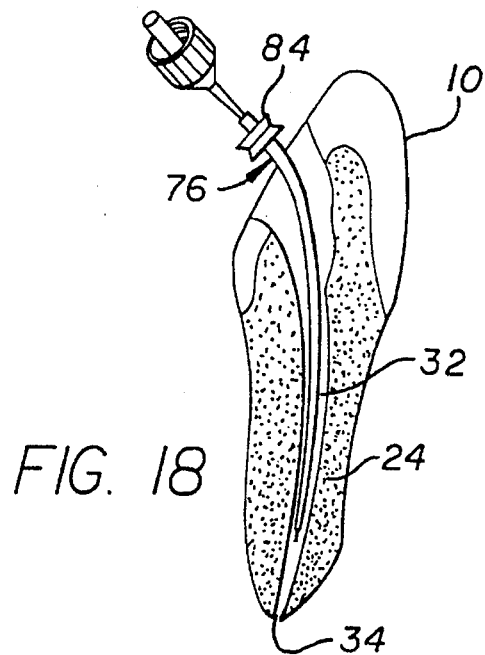
FIG. 18 illustrates another embodiment of the endodontic apparatus of the present invention called a fiber-optic root canal explorer for estimating the working length of the root canal.
Figure 19:
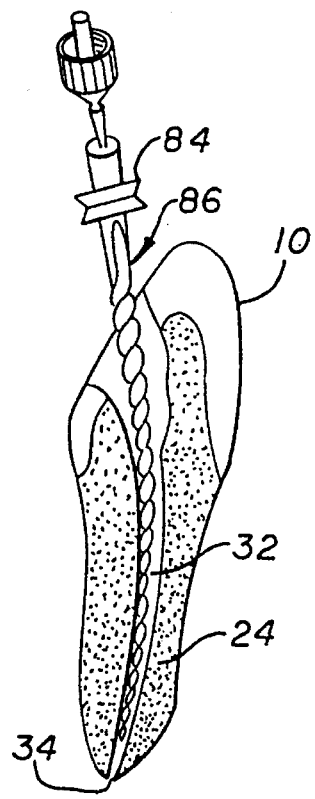
FIG. 19 illustrates the use of the fiber-optic reamer shown in FIG. 15 for shaving dentin to shape the root canal and for finding the end of the root canal during cleaning and shaping.

A root canal explorer 92 of the present invention is shown in FIG. 17. After opening the pulp chamber using conventional techniques, (i.e., using a round burr) the fiber-optic explorer is placed into the chamber to locate the entrance into the root canal 32. Based on the difference between fluorescence signals of the dentin 24 and the pulp 18, the root canal's entrance is identified. After the root canal is located, the fiber-optic file and reamer are carefully manipulated so as to clean and shape the root canal. (See FIGS. 18 and 19) During this procedure, the induced fluorescence from the components of the root canal are used to determine whether organic or infected tissue remain in the root canal. The apex 34 is detected by forwarding the fiber-optic tool towards the end of the root canal. Based on the fluorescence signal processing, a signal such as a voice or indicating light, warns that the apex of the canal has been reached. The conventional rubber stop 84 is used to assist in determining the correct working length of the tooth 10 prior to sealing the apex and filling the root canal using light cure restoratives.

Figure 20:
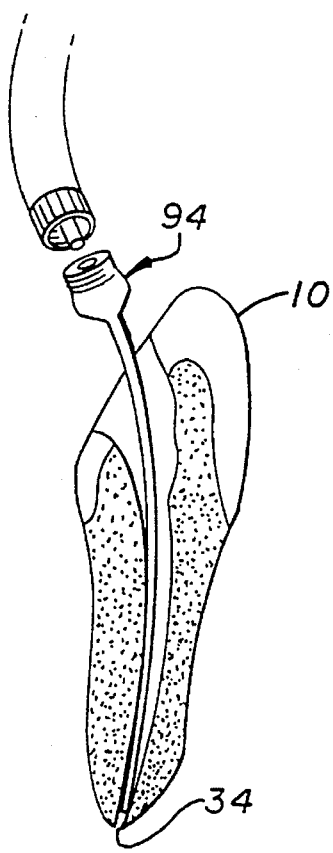
FIG. 20 illustrates another embodiment of the endodontic apparatus of the present invention called a fiber-optic apex locator for confirming the working length of the tooth using induced fluorescence.

A fiber-optic apex locator 94 of the present invention is shown in FIG. 20. The fiber-optic apex locator may be as simple as a fiber that extends to the apex 34 of the tooth 10. The apex locator may include a stop 84 to assist in determining the location of the apex.

Figure 21:
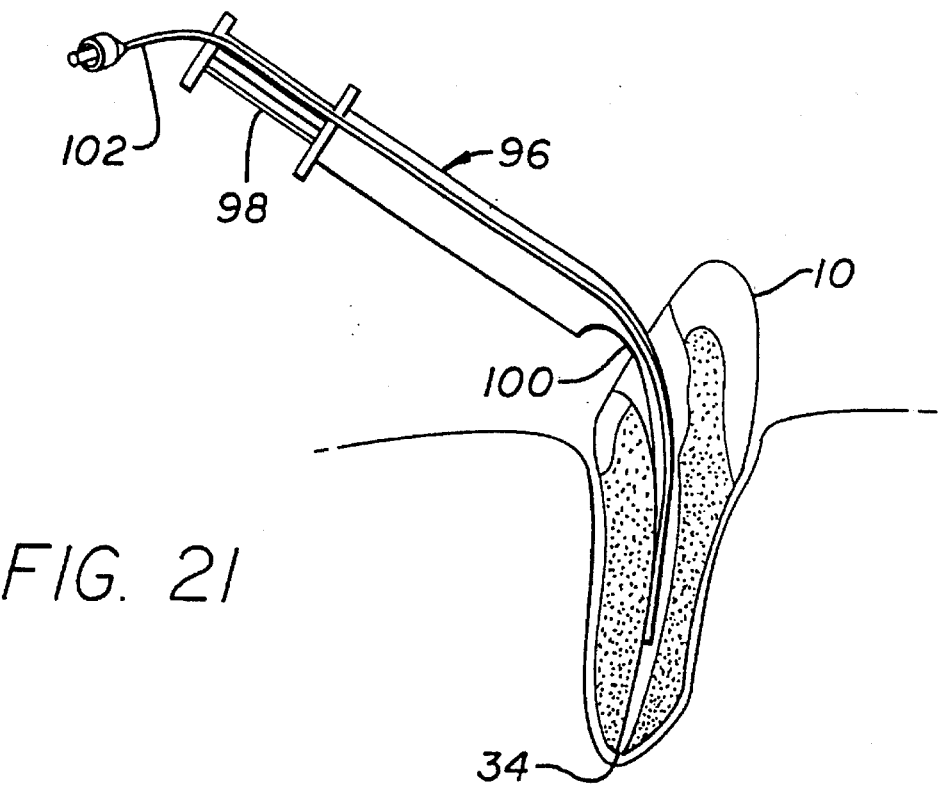
FIG. 21 illustrates a fiber-optic apex sealer of the present invention.

After cleaning the root canal 32, the apex 34 is sealed with light cure restoratives as shown in FIG. 21. The apex sealing apparatus 96 includes a plunger 98, a tube 100 and an optical fiber 102. The tube and the optical fiber extend to the apex of the root canal. The plunger is used to force light cure restorative through the tube. The light cure restorative is deposited at the apex of the root canal. The optical fiber delivers light to the apex to activate the light cure restorative.

Figure 22:
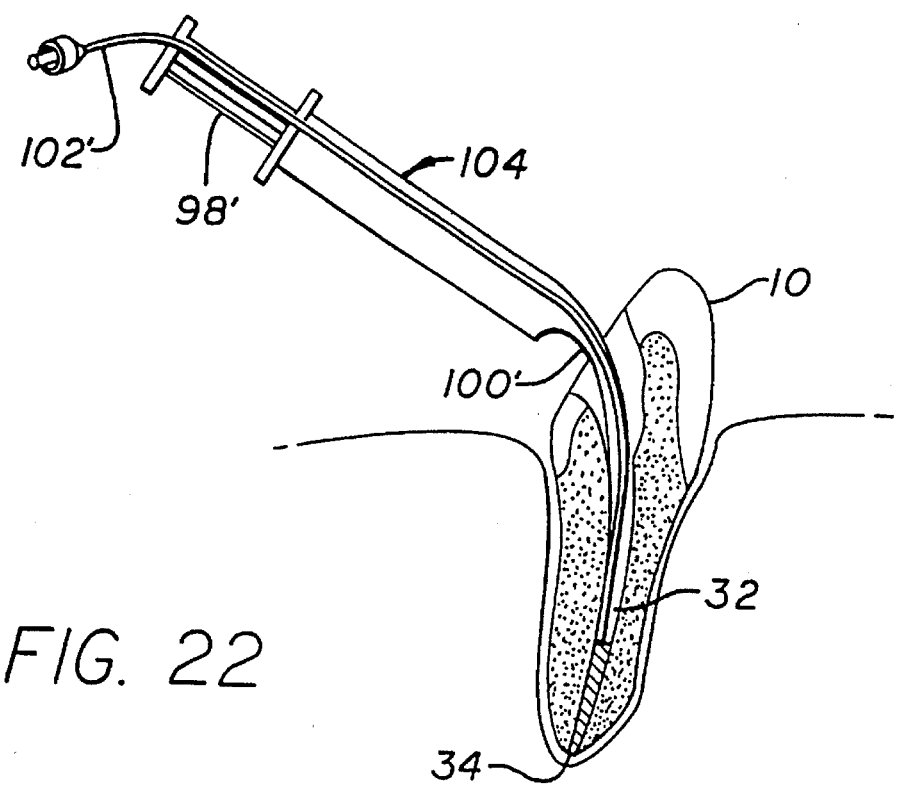
FIG. 22 and 23 illustrates a fiber-optic root canal filler of the present invention.
Figure 23:
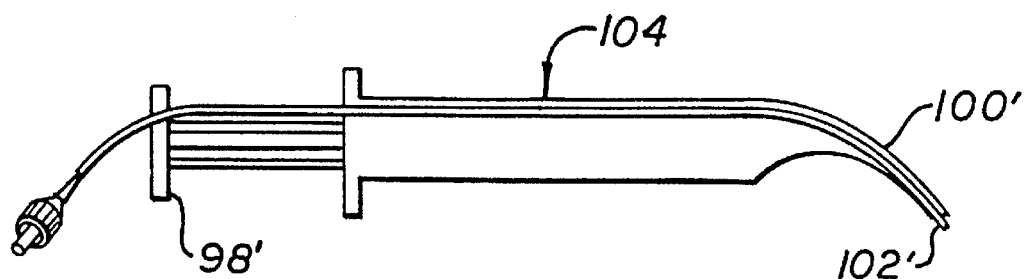

After the apex 34 has been sealed, the entire root canal 32 is filled with light cure restorative as shown in FIG. 22. The filling instrument 104 is shown in FIG. 23 and is similar in construction to the apex sealing apparatus 96, but the tube 100' is not required to extend completely to the apex of the tooth 10.

Figure 24:
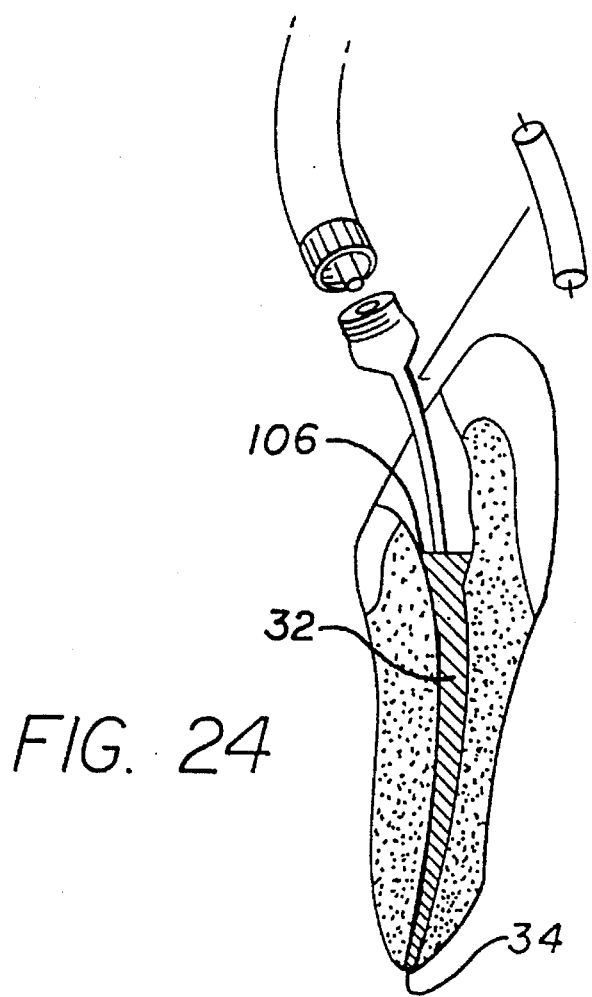
FIG. 24 illustrates the step of curing a light cure restorative in a root canal.
Figure 25:
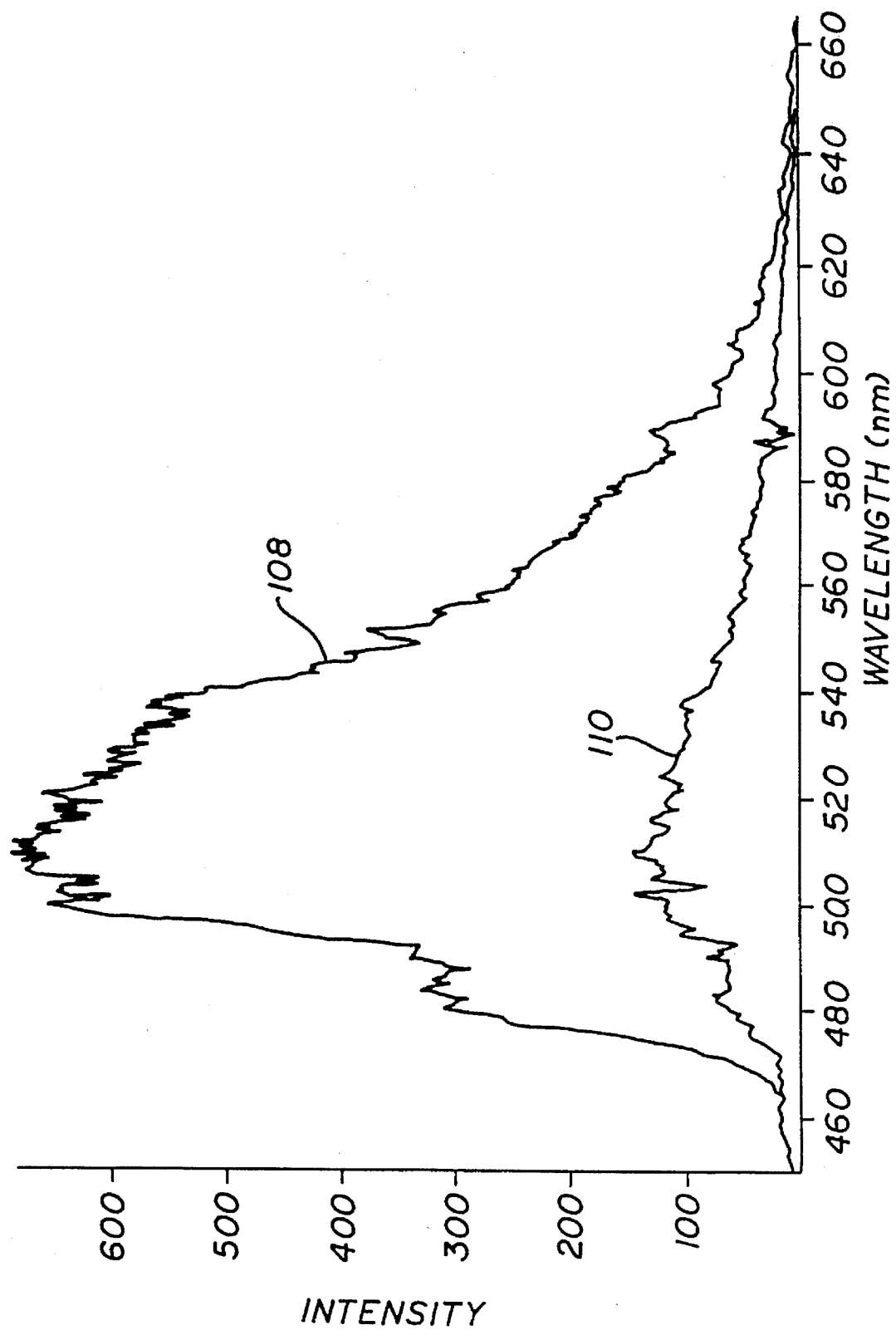
FIG. 25 is a graph of the intensity of fluorescence verses wavelength of light cure restorative before and after curing.

The fiber-optic induced fluorescence system is also suitable for detection of whether the light cure restorative 106 has actually cured. As shown in FIGS. 24 and 25, the fluorescence signal received from the light cure restorative, such as Silex Plus 3M®, before it is light activated 108 is much larger than the signal received after the restorative is activated by blue light and the compound polymerizes 110. This intensity decrease in a predetermined wavelength range, such as 500 to 540 nanometers, provides a feedback mechanism to control the root canal sealing and filling process and ensure that the sealing compound is properly cured. The curing process typically takes 1 to 5 minutes after the compound has been light activated.

A wide variety of fibers can be used in the present invention. The ultraviolet and visible light is readily transmitted through polymethylmethacrylate (PMMA0), polystyrene (PS) and silica-core fibers coated with silica, plastic clad silica and metal coated silica. Near-infrared light is readily transmitted through silica fibers. Mid-infrared (Tm:YAG,Ho:YAG) light is readily transmitted through low OH anhydroguide G Silica fiber. Erbium YAG or Er:YSGG (3,100 nanometers) light is readily transmitted through a zirconium fluoride fiber, however, flour is toxic.

If desired, the fiber-optic root canal tools and related methods discussed above may also be used to supplement conventional endodontic techniques of pre-procedure radiographs, tactile perception, average tooth length charts, etc. Thus, the dentist can choose the extent to which the fiber-optic tools are utilized.

From the foregoing, it will be appreciated that the endodontic tools and related methods discussed above tend to reduce the number of x-rays otherwise needed and used in conjunction with conventional instrument methods according to the skill and resources of the individual dentist. The endodontic tools clean and prepare the canal, thereby tending to reduce via folsas, and to minimize the dangers of broken instruments. The tools can establish the working length of the tooth, and locate the apex and seal the apex using light cure restoratives and/or high heat generated by light and fill the root canal with light cure restoratives. The tools also can eliminate pulp and pulp stones, and can cut, widen, and coagulate using infrared lasers through these same fiber-optic headpieces. In addition, the endodontic tools discussed above provide relatively instantaneous determination of the composition of the root canal without the processing delays associated with x-rays, etc.

Although the foregoing discloses preferred embodiments of the present invention, it is understood that those skilled in the art may make various changes to the preferred embodiments shown without departing from the scope of the invention. The invention is defined only by the following claims.

I claim:

1. An endodontic apparatus for determining and preparing a tooth's root canal, comprising:

a metal-coated optical fiber adapted to guide light between the ends of the fiber; and an elongated tool having first and second ends and a passage through its center between the first and second ends;

wherein the optical fiber passes through and is retained within the passage such that one end of the optical fiber is exposed at the first end of the tool; and wherein the first end of the tool is adapted to enter into the root canal.

2. An endodontic apparatus as defined in claim 1, wherein the optical fiber is adapted to guide ultraviolet, visible and infrared light.

3. An endodontic apparatus as defined in claim 1, further comprising a stop slidably mounted on the outer surface of the tool near the second end to the tool, the stop adapted to be used for determining the length of the root canal.

4. An endodontic apparatus for determining and preparing a tooth's root canal, comprising:

an optical fiber adapted to guide light between the ends of the fiber; and an elongated tool having first and second ends, and defining a passage through the tool's center between the first and second ends, wherein the optical fiber passes through and is retained within the passage such that one end of the optical fiber is exposed at the first end of the tool, and a slightly conical outside surface with the outside diameter of the tool being smaller at its first end than at its second end so that the first end of the tool is adapted to enter into the root canal, wherein the outside surface of the tool is a metal surface adapted to remove dentin from the tooth's root canal.

5. An endodontic apparatus as defined in claim 4, wherein the outside surface of the tool has flutes adapted to shave and remove dentin from the tooth's root canal.

6. An endodontic apparatus as defined in claim 4, wherein the outside surface of the tool has a tapered blank adapted to file and remove dentin from the root canal of a tooth.

7. An endodontic apparatus for determining and preparing a tooth's root canal, comprising:

an optical fiber adapted to guide light between the ends of the fiber; and an elongated tool having first and second ends and defining a passage through its center between the first and second ends, wherein the first end of the tool is adapted to enter into the root canal and the optical fiber passes through and is retained within the passage such that the one end of the optical fiber is exposed at the first end of the tool;

a light source adapted to emit excitation light that is directed into the one end of the optical fiber, wherein the excitation light is transmitted through the optical fiber to the first end of the tool to produce return light from the root canal which is captured at the first end of the tool by the optical fiber and transmitted to the other end of the optical fiber, such return light including fluorescent light from the tissues within the root canal;

a sensor for monitoring the return light received from the optical fiber and generating a plurality of electrical signals indicative of the intensity of return light within predetermined wavelength bands; and a processor adapted to process the plurality of signals and to thereby determine the composition of the root canal.

8. An endodontic apparatus as defined in claim 7, wherein:

the excitation light produced by the light source is narrowband light having a wavelength between 250 and 450 nanometers; and the predetermined wavelength bands associated with the plurality of electrical signals are within a wavelength range between 50 and 250 nanometers greater than the wavelength of the narrowband excitation light.

9. An endodontic apparatus as defined in claim 7, wherein:

the wavelength of the excitation light is about 442 nanometers; and the predetermined wavelength bands associated with the plurality of electrical signals include two reference bands and a peak band, the first reference band extending from about 500 nanometers to about 520 nanometers, the second reference band extending from about 620 nanometers to about 640 nanometers, and the peak band extending about plus and minus 10 nanometers from the wavelength associated with the intensity peak of the return light.

10. An endodontic apparatus as defined in claim 9, wherein the processor determines the composition of the root canal in accordance with a ratio defined by the formula:

$$\text{Ratio} = (S^{Peak} - S^{620-640})/(S^{500-520})$$

where $S^{Peak}$ is the intensity of light within the peak band, $S^{500-520}$ is the intensity of light within the first reference band, and $S^{620-640}$ is the intensity of light within the second reference band.

11. An endodontic apparatus as defined in claim 7, wherein the sensor includes:

a spectrograph having an array of detectors, the spectrograph resolving the return light such that each detector of the array detects a different spectral wavelength of the return light and generates a separate electrical signal representing the intensity of light in its wavelength; and an optical analyzer for analyzing the plurality of electrical signals from the spectrograph and generating the first and second signals.

12. An endodontic apparatus as defined in claim 7, wherein the processor includes an artificial neural network.

13. An endodontic apparatus as defined in claim 7, wherein the sensor comprises:

a dichroic filter that rejects the return light having a wavelength equal to the wavelength of the excitation light and transmits the return light within the predetermined wavelength bands;

a stop having a slit aperture, wherein a portion of the return light that is transmitted through the dichroic filter passes through the slit;

a grating adapted to spread the return light that passes through the slit such that the return light is spread along an axis by a distance proportional to the wavelength of the return light; and a plurality of electro-optical detectors for generating the plurality of electrical signals, respectively, each electro-optical detector located along the axis at a distance corresponding to the respective wavelength band.

14. An endodontic apparatus as defined in claim 7, further comprising a stop slidably mounted on the outer surface of the tool near the second end to the tool, the stop adapted to be used for determining the length of the root canal.

15. An endodontic apparatus as defined in claim 7, wherein:

the tool has a slightly conical outside surface such that the diameter of the tool is smaller at its first end than at its second end; and the outside surface of the tool is adapted to remove dentin from the tooth's root canal.

16. An endodontic apparatus as defined in claim 15, wherein the outside surface of the tool has metal flutes adapted to shave and remove dentin from the tooth's root canal.

17. An endodontic apparatus as defined in claim 15, wherein the outside surface of the tool has a metal tapered blank adapted to file and remove dentin from the root canal of a tooth.

18. Apparatus for locating the apex of a root canal, comprising:

a light source that emits excitation light;

an optical fiber that transmits the excitation light from the light source to tissues of a root canal to cause the tissues to produce return light, and that collects from the root canal return light which includes fluorescent light produced by the tissues illuminated by the excitation light;

a sensor that receives the return light from the optical fiber and generates signals indicative of the intensity of return light within predetermined wavelength bands; and a processor that processes the signals to identify the tissues within the root canal which have produced the return light to allow determination of the root canal's apex.

19. Apparatus for sealing the apex of a root canal with a light cure restorative, comprising:

a long hollow tube sized to fit within the root canal;

a plunger for forcing the light cure restorative through the tube and into the apex of the root canal;

an optical fiber for delivering light to the apex of the root canal to cure the light cure restorative.

20. Apparatus for filling a root canal with a light cure restorative, comprising:

a long hollow tube sized to fit within the rook canal:

a plunger for forcing a light cure restorative through the tube and into the root canal: and an optical fiber for delivering light inside the root canal to cure the light cure polymer.

21. A method of performing a root canal on a tooth, the tooth having a crown of enamel, a pulp chamber, and a root having the root canal, the method comprising:

creating an opening in the crown, removing the pulp from the pulp chamber, locating the root canal using induced fluorescence spectroscopy, cleaning and shaping the root canal using induced fluorescence spectroscopy;

locating the apex of the root canal using induced fluorescence spectroscopy;

preparing the apex of the root canal;

sealing the apex of the root canal using a light cure restorative;

filling the root canal using a light cure restorative.

22. A method of performing a root canal as defined in claim 21, wherein the step of sealing the apex includes the steps of:

placing a long hollow tube into the root canal until it extends to the apex;

forcing a light cure restorative through the tube and into the apex of the root canal; and sealing the apex of the root canal by delivering light to the apex of the root canal to activate the light cure restorative such that the light cure restorative cures.

23. A method of determining and preparing a tooth's root canal comprising:

directing excitation light into a tooth's root canal to produce return light, such return light including fluorescent light from the tissues within the root canal;

monitoring the return light and generating a plurality of electrical signals indicative of the intensity of return light within predetermined wavelength bands associated with the direct fluorescence of the tissues within the root canal; and processing the plurality of signals to determine structure of the root canal.

24. A method of determining and preparing a tooth's root canal as defined in claim 23, wherein:

the excitation light used in the step of directing is narrowband light having a wavelength between 250 and 450 nanometers; and the predetermined wavelength bands associated with the plurality of electrical signals used in the step of monitoring are at wavelengths between 50 and 250 nanometers greater than the wavelength of the narrowband excitation light.

25. A method of determining and preparing a tooth's root canal as defined in claim 23, wherein:

the wavelength of the excitation light used in the step of directing is about 442 nanometers; and the predetermined wavelength bands associated with the plurality of electrical signals used in the step of monitoring include two reference bands and a peak band, the first reference band extending from about 500 nanometers to about 520 nanometers, the second reference band extending from about 620 nanometers to about 640 nanometers, and the peak band extending about plus and minus 10 nanometers from the wavelength associated with the intensity peak of the return light.

26. A method of determining and preparing a tooth's root canal as defined in claim 25, wherein the step of processing includes determining the composition of the root canal in accordance with a ratio defined by the formula:

$$\text{Ratio} = (S^{Peak} - S^{620-640})/(S^{500-520})$$

where $S^{Peak}$ is the intensity of light with the peak band, $S^{500-520}$ is the intensity of light within the first reference band, and $S^{620-640}$ is the intensity of light within the second reference band.

27. A method of determining and preparing a tooth's root canal as defined in claim 23, wherein the step of processing includes providing a neural network.

28. A method of sealing the apex of a root canal with a light cure restorative, comprising:

placing a long hollow tube into the root canal until it extends to the apex;

forcing a light cure restorative through the tube and into the apex of the root canal; and sealing the apex of the root canal by delivering light to the apex of the root canal to activate the light cure restorative such that the light cure restorative cures.

29. A method of exploring a tooth's structure, the tooth including a crown which surrounds a pulp chamber and a root including a root canal therethrough, the root canal connecting the pulp chamber with an opening at the apex of the root, comprising:

providing an optical fiber having first and second ends, wherein the optical fiber is adapted to guide light between the first and second ends;

forming an opening through the tooth's crown to provide access to the tooth's pulp chamber and root canal;

placing the first end of the optical fiber through the opening formed in the tooth's crown and scanning within the interior of the pulp chamber using the first end to locate the entrance of the root canal;

directing excitation light into the second end of the optical fiber, guiding the excitation light from the second end of the optical fiber to the first end and emitting the excitation light from the first end of the optical fiber;

collecting return light at the first end of the optical fiber;

guiding the return light from the first end of the optical fiber to the second end and emitting the excitation light from the second end of the optical fiber;

monitoring the return light emitted from the second end of the optical fiber and generating a plurality of electrical signals indicative of the intensity of return light within predetermined wavelength bands; and processing the plurality of signals to identify the entrance of the root canal.

30. A method of exploring a tooth's structure, the tooth including a crown which surrounds a pulp chamber and a root including a root canal therethrough, the root canal connecting the pulp chamber with an opening at the apex of the root, comprising:

providing an optical fiber having first and second ends, wherein the optical fiber is adapted to guide light between the first and second ends;

forming an opening through the tooth's crown to provide access to the tooth's pulp chamber and root canal;

placing the first end of the optical fiber through the opening formed in the tooth's crown and probing within the root canal using the first end to locate the apex of the root canal;

directing excitation light into the second end of the optical fiber, guiding the excitation light from the second end of the optical fiber to the first end and emitting the excitation light from the first end of the optical fiber;

collecting return light at the first end of the optical fiber;

guiding the return light from the first end of the optical fiber to the second end and emitting the excitation light from the second end of the optical fiber;

monitoring the return light emitted from the second end of the optical fiber and generating a plurality of electrical signals indicative of the intensity of return light within predetermined wavelength bands; and processing the plurality of signals to determine the location of the apex of the root canal.

31. A method of determining and preparing a tooth's root canal comprising:

directing excitation light having a wavelength of about 442 nanometers into a tooth's root canal to produce return light, such return light including fluorescent light from the tissues within the root canal;

monitoring the return light and generating a plurality of electrical signals indicative of the intensity of return light within predetermined wavelength bands associated with the direct fluorescence of the tissues within the root canal, wherein the predetermined wavelength bands include two reference bands and a peak band, the first reference band extending from about 500 nanometers to about 520 nanometers, the second reference band extending from about 620 nanometers to about 640 nanometers, and the peak band extending about plus and minus 10 nanometers from the wavelength associated with the intensity peak of the return light; and determining the structure and composition of the root canal by processing the electrical signal associated with the two reference bands and the peak band in accordance with a ratio defined by the formula:

$$\text{Ratio} = (S^{Peak} - S^{620-640})/(S^{500-520})$$

where $S^{Peak}$ is the intensity of light with the peak band, $S^{500-520}$ is the intensity of light within the first reference band, and $S^{620-420}$ is the intensity of light within the second reference band.

* * * * *